US006271222B1

(12) United States Patent
Dininno

(10) Patent No.: US 6,271,222 B1
(45) Date of Patent: *Aug. 7, 2001

(54) PENEM ANTIBACTERIAL COMPOUNDS, COMPOSITIONS AND METHODS OF TREATMENT

(75) Inventor: Frank P. Dininno, Old Bridge, NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/298,223

(22) Filed: Apr. 23, 1999

Related U.S. Application Data

(60) Provisional application No. 60/087,012, filed on May 28, 1998.

(51) Int. Cl.[7] .................... C07D 499/887; A61K 31/431; C07F 7/18; A61P 31/04

(52) U.S. Cl. .......................... 514/192; 514/195; 540/310

(58) Field of Search ............................ 540/310; 514/192, 514/195

(56) References Cited

U.S. PATENT DOCUMENTS

| | | | |
|---|---|---|---|
| 4,479,947 | 10/1984 | Christensen | 424/203 |
| 5,703,068 * | 12/1997 | Iwata | 540/310 |

FOREIGN PATENT DOCUMENTS

| | | |
|---|---|---|
| 0 007 614 A1 | 2/1980 | (EP) . |
| 0 072 014 | 2/1983 | (EP) . |
| 0 416 953 A2 | 7/1990 | (EP) . |
| 0 507 313 A1 | 10/1992 | (EP) . |
| WO 95/23149 | 8/1995 | (WO) . |

OTHER PUBLICATIONS

A. J. Corraz et al., *J. Med. Chem.*, 35 p 1828–1839 (1992).

P. D. Jeffrey and S. W. McCombie, *J. Org. Chem.*, 47, p 587–590 (1982).

* cited by examiner

*Primary Examiner*—Mark L. Berch
(74) *Attorney, Agent, or Firm*—Sylvia A. Ayler; Mark R. Daniel

(57) ABSTRACT

The present invention relates to penem antibacterial agents in which the releaseable liphophilic aromatic side-chain, tethered to the carbapenem nucleus via a methylene linker, necessary for anti-MRSA activity replaces the non-releaseable liphophilic side-chains found in 2-aryl and 2-benzothiazolylthio carbapenem compounds. The compound is further substituted with various substituent groups including at least one cationic group.

The compounds are represented by formula I:

I

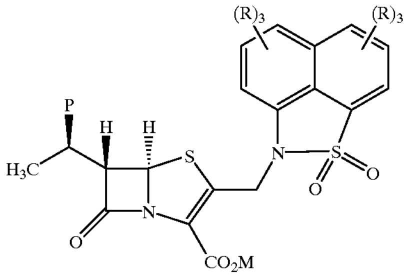

Pharmaceutical compositions and methods of use are also included.

26 Claims, No Drawings

PENEM ANTIBACTERIAL COMPOUNDS, COMPOSITIONS AND METHODS OF TREATMENT

This application claims the benefit of U.S. Provisional Application No. 60/087,012, filed May 28, 1998.

BACKGROUND OF THE INVENTION

Infections caused by methicillin resistant *Staphylococcus aureus* (MRSA) and related gram positive pathogens are a growing medical concern. Vancomycin, a glycopeptide antibiotic, is currently the agent of choice for combating these infections which are predominantly encountered in hospital settings. With the increased usage of Vancomycin, the emergence of resistant stains of staphylococci is inevitable, and the first confirmed report of vancomycin resistance in *Staphylococcus epidermidis* was disclosed at the 36th Interscience Conference on Antimicrobial Agents and Chemotherapy, New Orleans, La., 1996. Consequently, there is a dire need to develop new agents with an alternative mode of action.

The present invention relates to novel penem compounds in which the releaseable liphophilic aromatic side-chain, tethered to the penem nucleus via a methylene linker, necessary for anti-MRSA activity replaces the non-releaseable liphophilic side-chains found in 2-aryl and 2-benzothiazolylthio carbapenem compounds. The present invention replaces the common simple ether based found in EPO 416,953, substituted carbon atoms found in EPO 507,313, and substituted amines found in WO 9523149. The antibacterial compounds of the present invention thus comprise an important contribution to therapy for treating infections caused by these difficult to control pathogens. There is an increasing need for agents effective against such pathogens (MRSA/MRCNS) which are at the same time relatively free from undesirable side effects.

SUMMARY OF THE INVENTION

The present invention relates to anti-MRSA penem antibiotics containing releaseable aromatic based side-chains. The releaseable side-chain imparts MRSA activity by preventing or lessening the likelihood of immune-mediated toxicity previously associated with the 2-aryl linked and 2-benzothiazolylthio carbapenems.

The compounds of the invention are represented by formula

I

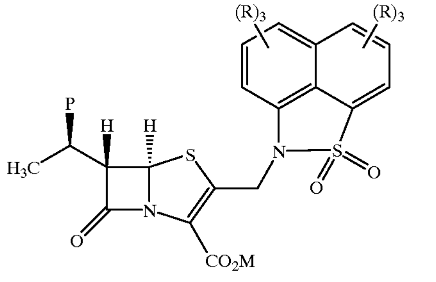

or a pharmaceutically acceptable salt thereof, wherein:

$CO_2M$ represents a carboxylic acid, a carboxylate anion or cation, a pharmaceutically acceptable ester group or a carboxylic acid protected by a protecting group;

P represents hydrogen, hydroxyl, fluoro or hydroxyl protected by a hydroxyl-protecting group;

each R is independently selected from: —R*; A—$(CH_2)_n$—Q; —Q; hydrogen; halo; —CN; —$NO_2$; —$NR^aR^b$; —$OR^c$; —$SR^c$; —C(O)$NR^aR^b$; —C(O)$OR^h$; —S(O)$R^c$; —$SO_2R^c$; —$SO_2NR^aR^b$; —$NR^aSO_2R^b$; —C(O)$R^a$; —OC(O)$R^a$; —OC(O)$NR^aR^b$; —$NR^aC(O)NR^bR^c$; —$NR^aCO_2R^h$; —$OCO_2R^h$; —$NR^aC(O)R^b$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups;

A represents O, S or $CH_2$; n=0–3;

each $R^a$, $R^b$ and $R^c$ independently represents hydrogen, —R*, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —R* or —Q;

wherein when —$OR^g$ is OH, the OH group can be optionally protected by a hydroxyl protecting group;

$R^e$, $R^f$ and $R^g$ represent hydrogen; —R*; —$C_{1-6}$ straight- or branched-chain alkyl unsubstituted or substituted with one to four $R^i$ groups;

or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)_3$; —C(O)$N(R^h)_2$; —$SO_2N(R^h)_2$; heteroaryl; heteroarylium; —$CO_2R^h$; —C(O)$R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$–$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

Q is selected from the group consisting of:

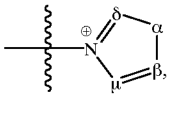 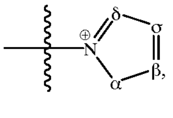 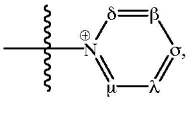

-continued

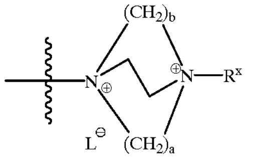

and

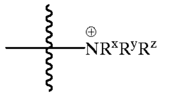

wherein:

a and b are 1, 2 or 3;

$L^-$ is a pharmaceutically acceptable counterion;

α represents O, S or $NR^s$;

β, δ, λ, μ and σ represent $CR^t$, N or $N^+R^s$, provided that no more than one of β, δ, λ, μ and σ is $N^+R^s$;

$R^*$ is selected from the group consisting of:

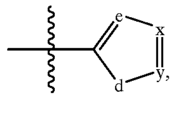

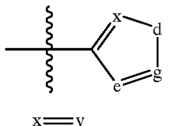

and

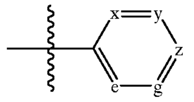

wherein:

d represents O, S or $NR^k$;

e, g, x, y and z represent $CR^m$, N or $N^+R^k$, provided that no more than one of e, g, x, y and z in any given structure represents $N^+R^k$;

$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;

each $R^m$ independently represents a member selected from the group consisting of: hydrogen; halo; —CN; —$NO_2$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; —$NR^nCO_2R^h$; —$NR^nCONR^oR^h$; —$OCO_2R^h$; —$CNR^nNR^oR^h$; —$NR^nCNHNR^oR^h$; —$NR^nC(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_n$ Q where n and Q are as defined above;

$R^n$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4–6 membered saturated ring optionally interrupted by one or more of O, S, $NR^w$ or —C(O)—, said ring being unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

or $R^h$ and $R^w$ taken together with any intervening atoms represent a 5–6 membered saturated ring, optionally interrupted by one or two of O, S, $SO_2$, NH or $NCH_3$;

$R^x$ represents hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heterary1, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

or $R^x$ and $R^y$ together with any intervening atoms represent a 4–6 membered saturated ring optionally interrupted by O, S, $SO_2$, $NR^w$, $N^+R^hR^w$ or —C(O)—, unsubstituted or substituted with 1–4 $R^i$ groups, and when $R^x$ and $R^y$ together represent a 4–6 membered ring as defined above, $R^z$ is as defined above or $R^z$ represents an additional saturated 4–6 membered ring fused to the ring represented by $R^x$ and $R^y$ taken together, optionally interrupted by O, S, $NR^w$ or —C(O)—, said rings being unsubstituted or substituted with one to four $R^i$ groups.

Pharmaceutical compositions and methods of treatment are also included herein.

DETAILED DESCRIPTION OF THE INVENTION

The invention is described herein in detail using the terms defined below unless otherwise specified.

Carboxylate anion refers to a negatively charged group —COO—.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, selected from $R^d$ and $R^i$, as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

pyrrole (pyrrolyl)

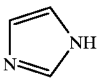
imidazole (imidazolyl)

thiazole (thiazolyl)

oxazole (oxazolyl)

furan (furyl)

thiophene (thienyl)

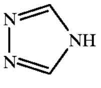
triazole (triazolyl)

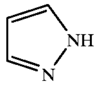
pyrazole (pyrazolyl)

isoxazole (isoxazolyl)

isothiazole (isothiazolyl)

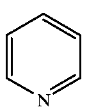
pyridine (pyridinyl)

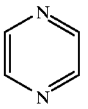
pyrazine (pyrazinyl)

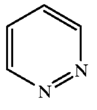
pyridazine (pryidazinyl)

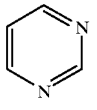
pyrimidine (pyrimidinyl)

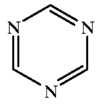
triazine (triazinyl)

Heteroarylium refers to heteroaryl groups bearing a quaternary nitrogen atom and thus a positive charge. Examples include the following:

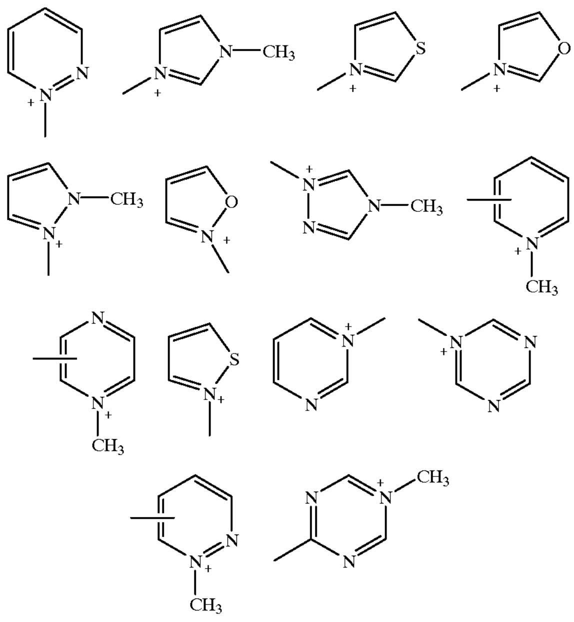

When a charge is shown on a particular nitrogen atom in a ring which contains one or more additional nitrogen atoms, it is understood that the charge may reside on a different nitrogen atom in the ring by virtue of charge resonance that occurs.

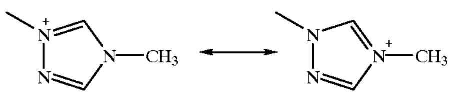
and

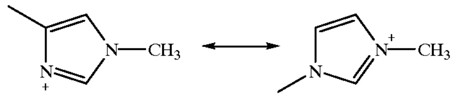

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e. g. tetramethylammonium), heteroarylium, (e.g., N-methylpyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

Alkoxy refers to $C_1$–$C_4$ alkyl-O—, with the alkyl group optionally substituted as described herein.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

In some of the penem compounds of the present invention, M is a readily removable carboxyl protecting group, and/or P represents a hydroxyl which is protected by a hydroxyl-protecting group. Such conventional protecting groups consist of known groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBS), phenacyl, p-methoxybenzyl, o-nitrobenzyl, p-methoxyphenyl, p-nitrobenzyl, 4-pyridylmethyl and t-butyl.

Examples of suitable hydroxyl protecting groups include triethylsilyl (TES), t-butyldimethylsilyl(TBS), t-butyldiphenylsilyl (DPTBS), o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The penem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —$CO_2M$, which is attached to the penem nucleus at position 3, this represents a carboxylic acid group (M represents H), a carboxylate anion (M represents a negative charge), a carboxylate cation (M represents a positive charge only when Q is absent), a pharmaceutically acceptable ester (M represents an ester forming group) or a carboxylic acid protected by a protecting group (M represents a carboxyl protecting group). The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intestinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

$L^-$ can be present or absent as necessary to maintain the appropriate charge balance. When present, $L^-$ represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate, tosylate, and trifluoromethanesulfonate. Other suitable anionic species will be apparent to the ordinarily skilled chemist.

Likewise, when $L^-$ represents a specie with more than one negative charge, such as malonate, tartrate or ethylenediaminetetraacetate (EDTA), an appropriate number of carbapenem molecules can be found in association therewith to maintain the overall charge balance and neutrality.

A subset of compounds of formula I which is of interest relates to those compounds where $CO_2M$ represents a carboxylate anion. Hence, M in this instance represents a negative charge which will be balanced by a positively charged group, such as in a positively charged R group. Likewise, if the positively charged R group contains more than one positive charge, a negatively charged counterion may be present which in combination with the carboxylate anion, provides overall charge neutrality.

Another subset of compounds of formula I which is of interest relates to compounds wherein one R represents a group which contains a positively charged moiety, and the remaining R groups are selected from hydrogen and $C_{1-6}$ straight or branched chain alkyl, unsubstituted or substituted with one to four $R^d$ groups. More particularly, this subset of interest includes compounds of formula Ia wherein one R represents a group containing a positively charged moiety and the remaining R groups are hydrogen.

With respect to the positively charged moiety or moieties that are contained in one or more R groups, it is preferred that from 1–3 positive charges be present, and most preferably two positive charges be present, balanced by the carboxylate anion and a negatively charged counterion.

Another subset of compounds which is of interest is represented by formula I wherein one R group represents a —$C_{1-6}$ straight or branched chain alkyl group, substituted with one to four $R^d$ groups, wherein one $R^d$ group represents —R* or Q. Hence, a positively charged moiety —R* or Q is attached to an alkyl group.

Another group of compounds of interest is represented by formula I wherein Q is selected from the group consisting of:

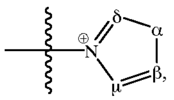 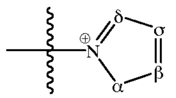 and

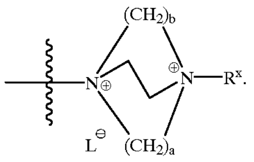

More particularly, the group of compounds which is of interest is represented by formula I wherein Q represents:

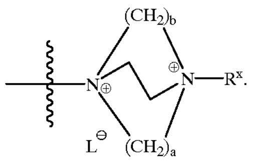

Within this subset of compounds, $L^-$, a and b are as originally defined, and $R^x$ is as originally defined, and represents a member selected from the group consisting of: hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups.

Another group of compounds of interest is represented by formula I wherein Q represents —$N^+R^xR^yR^z$, wherein $R^x$, $R^y$ and $R^z$ are as originally defined.

Another group of compounds of interest is represented by formula I wherein one R* group is present and is selected from:

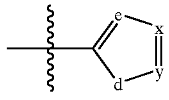 and 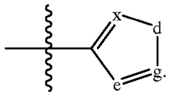

Within this subset, d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Another group of compounds of interest is represented by formula I wherein R is A—$(CH_2)_n$—Q, wherein A and Q are as originally defined.

A preferred subset of compounds of formula I which is of particular interest relates to compounds represented by formula Ia Ia

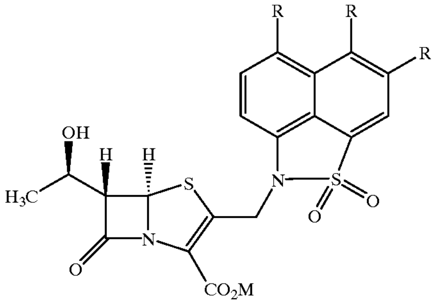

wherein:

$CO_2M$ represents a carboxylate anion;

one R group which is attached to the naphthosultam platform contains at least one positively charged moiety, and the remaining R groups are selected from hydrogen and $C_{1-6}$ straight or branched chain alkyl, unsubstituted or substituted with one to four $R^d$ groups;

$R^d$ is as originally defined;

$R^h$ represents hydrogen or a $C_{1-6}$ straight or branched chain alkyl group;

Q is selected from the group consisting of:

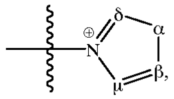 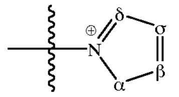 and

-continued

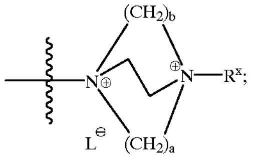

wherein $L^-$, a and b are as originally defined, and $R^x$ represents a member selected from the group consisting of: hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^h$C(O)$R^w$, $NR^h$C(O)$NR^hR^w$, phenyl or heteroaryl, said phenyl or heteroaryl group being optionally substituted with from one to four $R^i$ groups or with one to two $C_{1-3}$ straight- or branched-chain alkyl groups, said alkyl groups being unsubstituted or substituted with one to four $R^i$ groups;

R* is selected from:

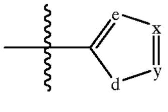

and

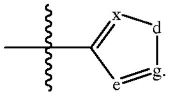

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Within this subset, all other variables are as originally defined with respect to formula I.

Another more preferred subset of compounds is represented by formula Ib:

Ib

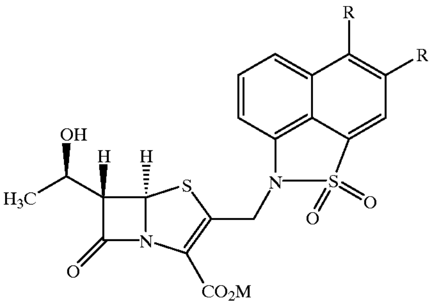

or a pharmaceutically acceptable salt thereof, wherein:

$CO_2M$ represents a carboxylate anion;

one R group is attached to the naphthosultam platform which contains a positively charged moiety, and the other R group is selected from hydrogen and $C_{1-6}$ straight or branched chain alkyl, unsubstituted or substituted with one to four $R^d$ groups;

$R^d$ is as originally defined;

Q is selected from the group consisting of:

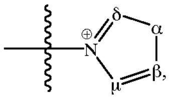

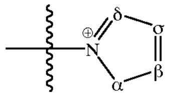

and

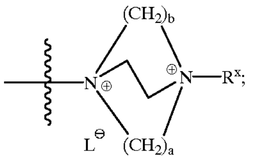

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^h$C(O)$R^w$, $NR^h$C(O)$NR^hR^w$, phenyl or heteroaryl, said phenyl and heteroaryl group being optionally substituted with from one to four $R^i$ groups or with one to two $C_{1-3}$ straight- or branched-chain alkyl groups, said alkyl groups being unsubstituted or substituted with one to four $R^i$ groups;

$R^h$ represents hydrogen or a $C_{1-6}$ straight or branched chain alkyl group;

$R^w$ is as originally defined;

R* is selected from:

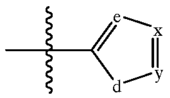

and

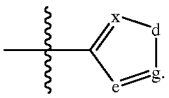

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen. Within this subset, all other variables are as originally defined with respect to formula I.

Another more preferred subset of compounds is represented by formula Ic:

Ic

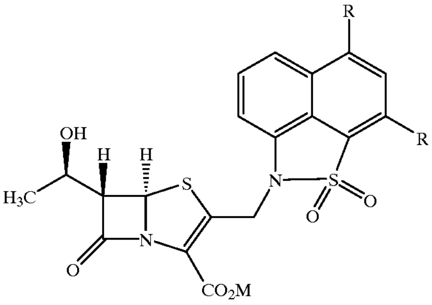

or a pharmaceutically acceptable salt thereof, wherein:

$CO_2M$ represents a carboxylate anion;

one R group is attached to the naphthosultam platform which contains a positively charged moiety, and the other R group is selected from hydrogen, halo and $C_{1-6}$ straight or branched chain alkyl, unsubstituted or substituted with one to four $R^d$ groups;

$R^d$ is as originally defined;

Q is selected from the group consisting of:

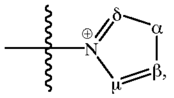
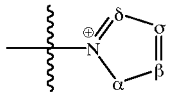
and

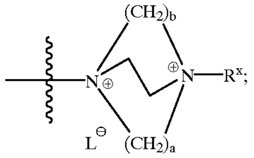

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2$ $R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

$R^h$ represents hydrogen or a $C_{1-6}$ straight or branched chain alkyl group;

$R^w$ is as originally defined;

R* is selected from:

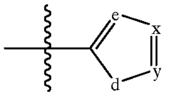
and
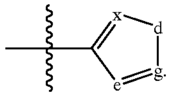

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen. Within this subset, all other variables are as originally defined with respect to formula I.

Another more preferred subset of compounds is represented by formula Id:

Id

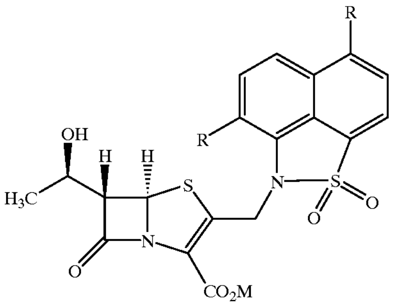

or a pharmaceutically acceptable salt thereof, wherein:

$CO_2M$ represents a carboxylate anion;

one R group is attached to the naphthosultam platform which contains a positively charged moiety, and the other R group is selected from hydrogen, halo and $C_{1-6}$ straight or branched chain alkyl, unsubstituted or substituted with one to four $R^d$ groups;

$R^d$ is as originally defined;

Q is selected from the group consisting of:

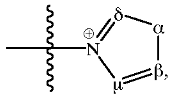
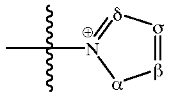
and

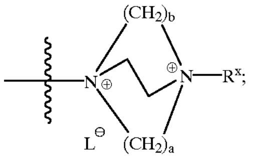

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2$ $R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight- or branched-chain alkyl groups, said alkyl groups being unsubstituted or substituted with one to four $R^i$ groups;

$R^h$ represents hydrogen or a $C_{1-6}$ straight or branched chain alkyl group;

$R^w$ is as originally defined;

R* is selected from:

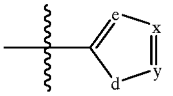
and
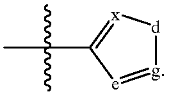

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen. Within this subset, all other variables are as originally defined with respect to formula I.

Still more preferably, the present invention relates to a compound represented by formula Ia wherein the R group at position 4 represents a positively charged moiety, and the R groups at position 3 and 5 represent hydrogen.

In particular, such compounds can be represented by formula Ie:

Ie

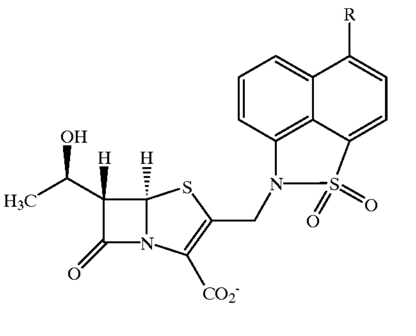

or a pharmaceutically acceptable salt thereof, wherein:

R contains a positively charged moiety selected from the group consisting of: —R*, Q, A—$(CH_2)_n$—Q, and a $C_{1-6}$ straight or branched alkyl chain substituted with one $R^d$ group, wherein A is as originally described;

$R^d$ is independently selected —R* or Q;

Q is selected from the group consisting of:

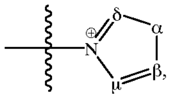

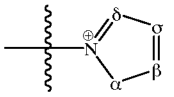

and

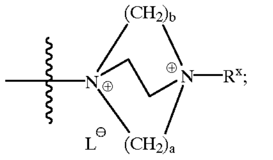

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

R* is selected from:

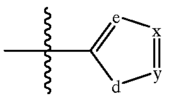

and

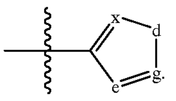

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Likewise, such compounds can be represented by formula If:

If

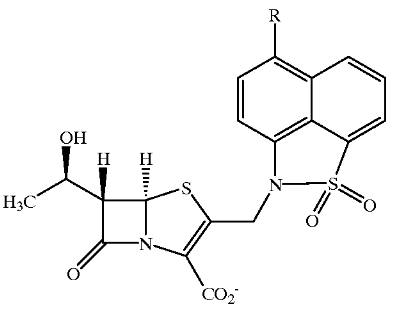

or a pharmaceutically acceptable salt thereof, wherein:

R contains a positively charged moiety selected from the group consisting of: —R*, Q, A—$(CH_2)_n$—Q, and a $C_{1-6}$ straight or branched alkyl chain substituted with one $R^d$ group, wherein A is as originally described;

$R^d$ is independently selected —R* or Q;

Q is selected from the group consisting of:

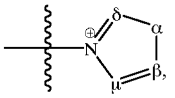

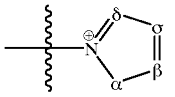

and

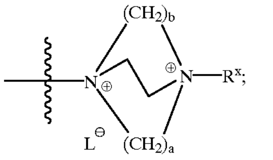

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

R* is selected from:

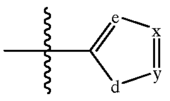

and

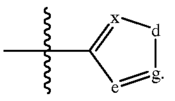

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

A still more preferred subset of compounds of the invention is represented by formula Ie wherein:

R represents

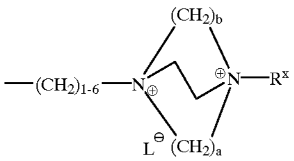

and $R^x$, a, b and $L^-$ are as originally defined.

Another more preferred subset of compounds of the invention is represented by formula Ig:

Ig

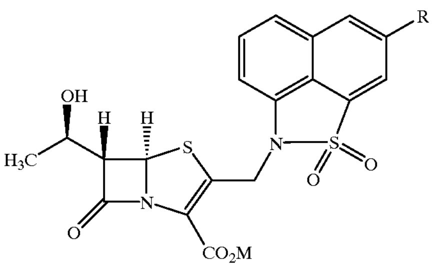

wherein:

R represents

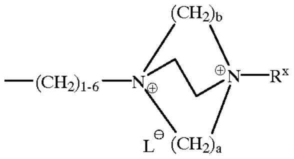

and $R^x$, a, b and $L^-$ are as originally defined.

Another more preferred subset of the compounds of formula Ig is realized when:

R represents A—$(CH_2)_n$—Q, wherein A is $CH_2$ and Q is selected from the group consisting of:

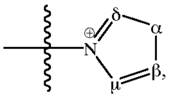

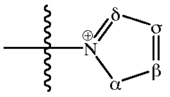

and

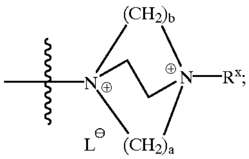

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups.

Within the subsets, all other variables are as originally defined with respect to formula I.

Representative examples (Tables 1–21) of compounds of the invention are shown below. The invention is intended, where appropriate, to include protonated amines protonated at the appropriate pH, e.g., pH 7.

TABLE 1

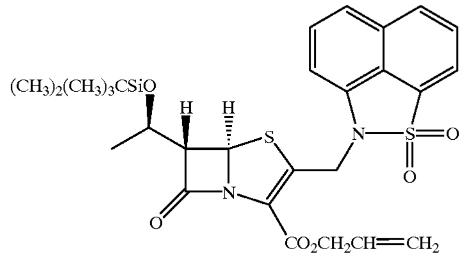

A-1

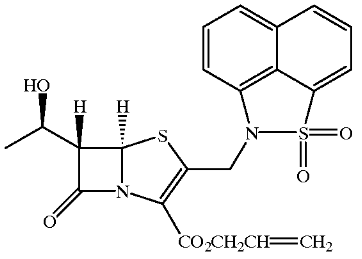

A-2

TABLE 1-continued
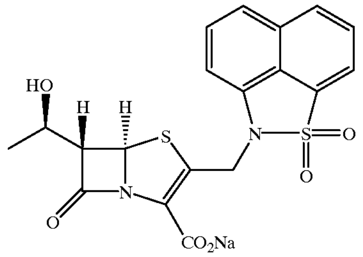
A-3
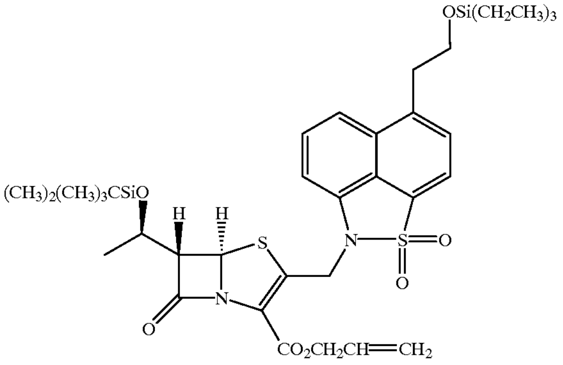
A-4
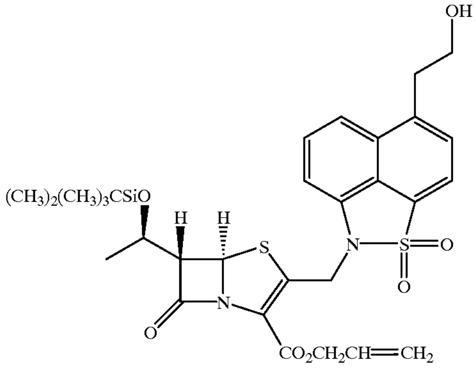
A-5
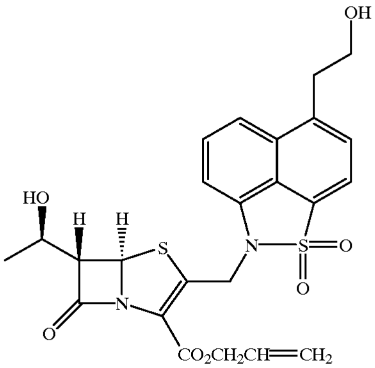
A-6

TABLE 1-continued
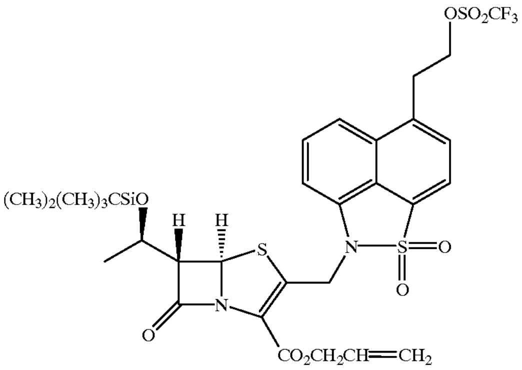
A-7
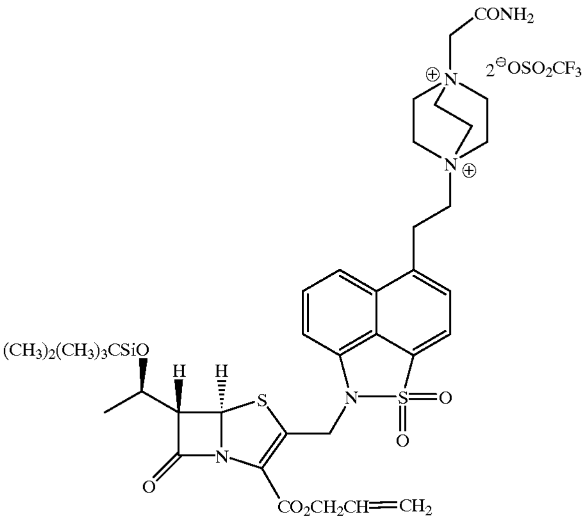
A-8
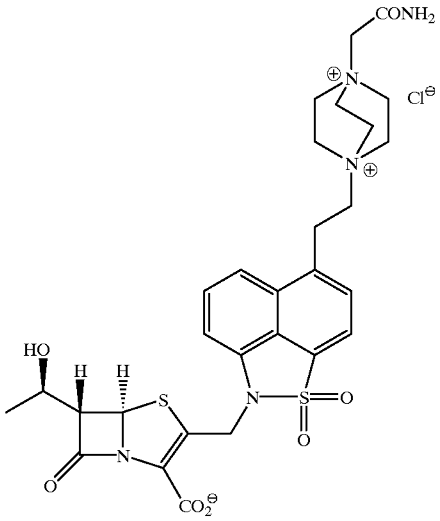
A-9

TABLE 1-continued
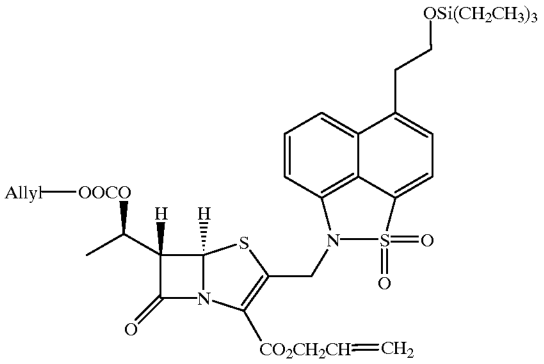
A-10
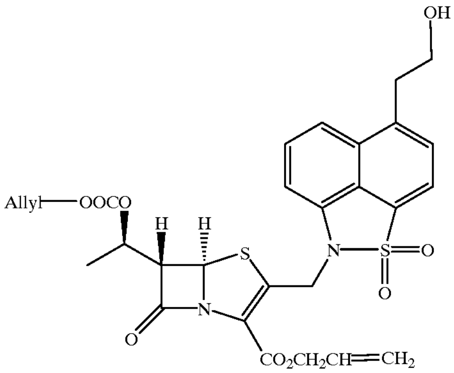
A-11
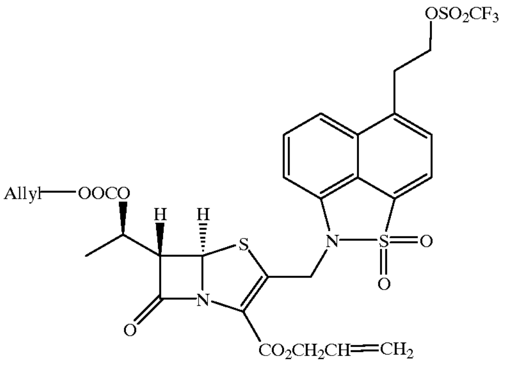
A-12

TABLE 1-continued
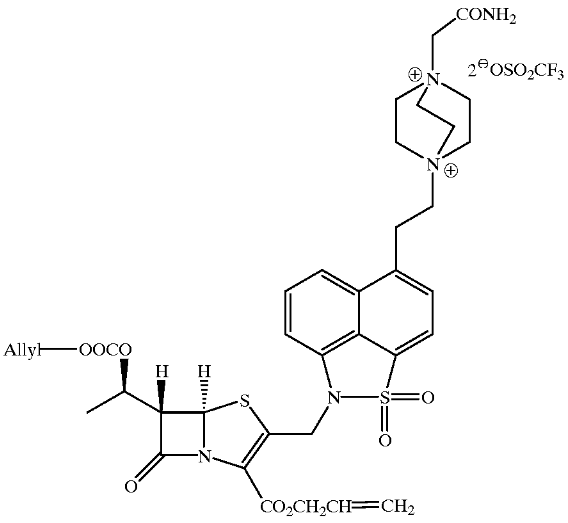
A-13
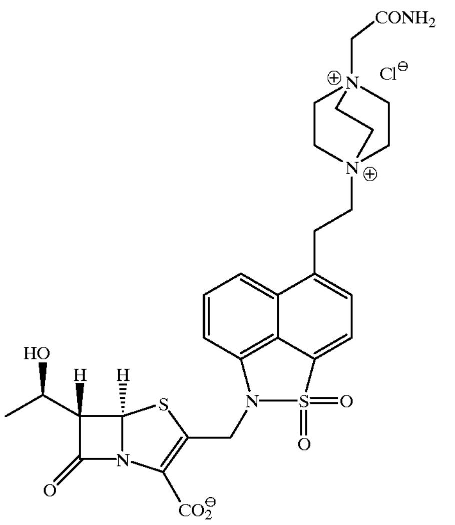
A-14
TABLE 2
E-1
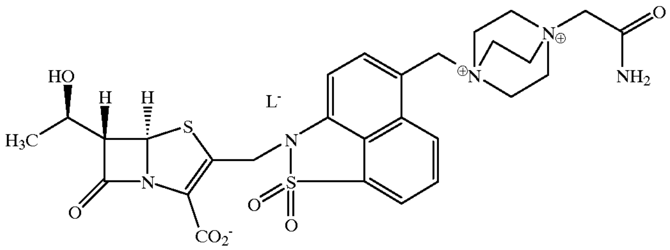
and
L⁻

TABLE 2-continued
E-2
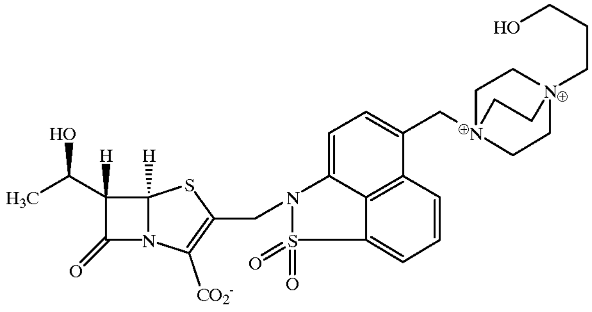
E-3
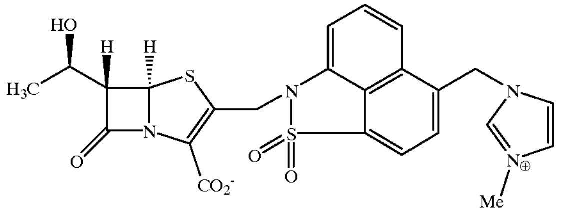
E-4
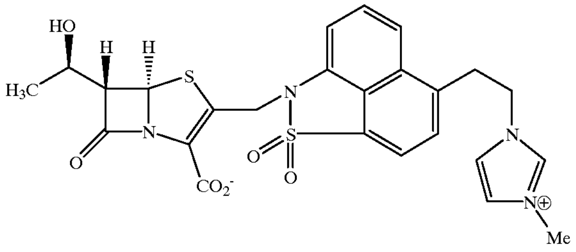
E-5
$L^-$
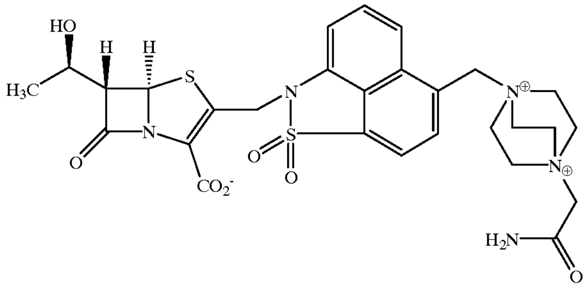
E-7
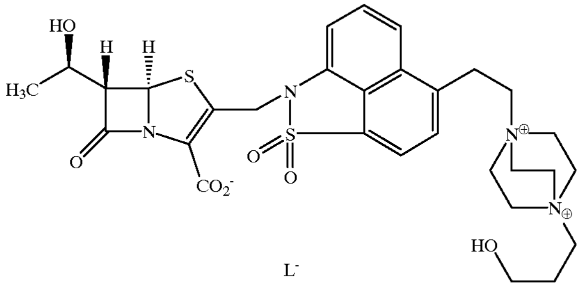
$L^-$ TABLE 2-continued
E-6
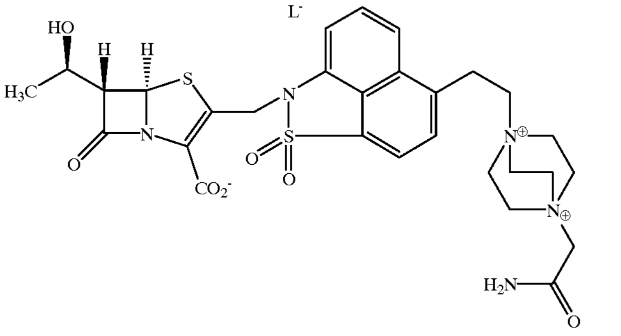
E-8
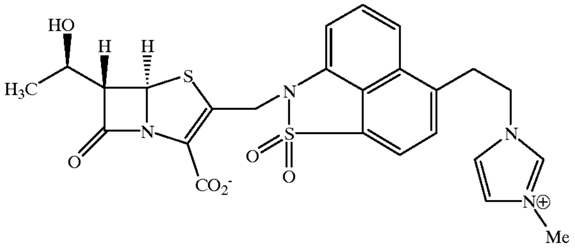
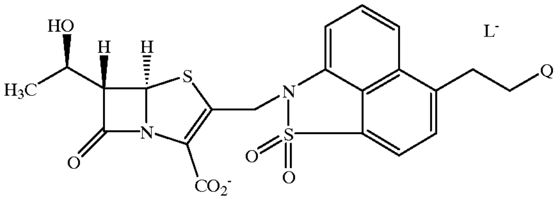
TABLE 3
| # | Q | # | Q | # | Q |
|---|---|---|---|---|---|
| 9 | 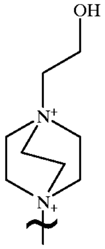 | 10 | 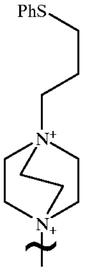 Ph = phenyl | 11 | 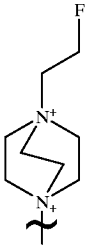 |

TABLE 3-continued
| # | Q | # | Q | # | Q |
|---|---|---|---|---|---|
| 12 | 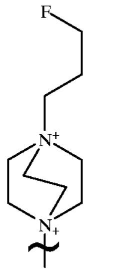 | 13 | 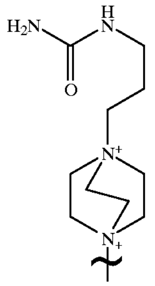 | 14 | 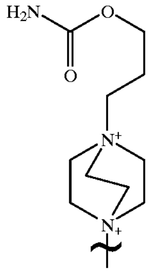 |
| 15 | 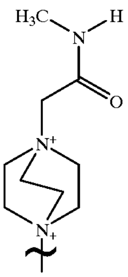 | 16 | 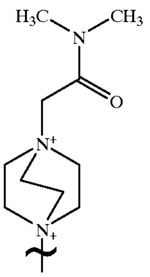 | 17 | 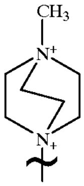 |
| 18 | 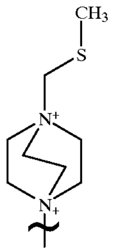 | 19 | 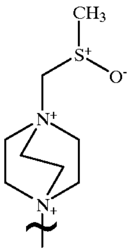 | 20 | 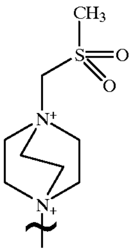 |
| 21 | 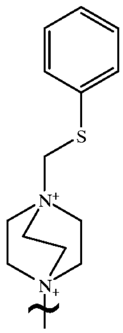 | 22 | 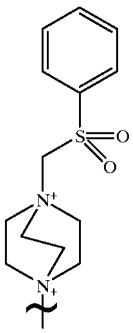 | 23 | 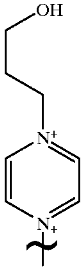 |

TABLE 3-continued
| # | Q | # | Q | # | Q |
|---|---|---|---|---|---|
| 24 | 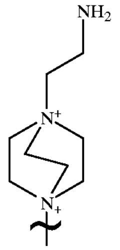 | 25 | 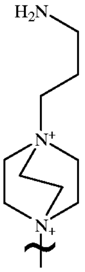 | 26 | 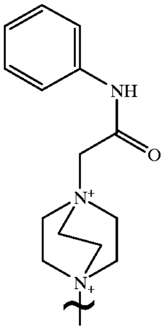 |
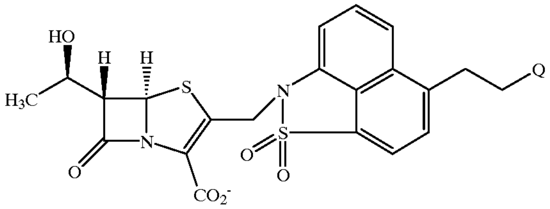
TABLE 4
| # | Q | # | Q | # | Q |
|---|---|---|---|---|---|
| 27 | 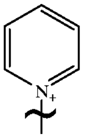 | 28 | 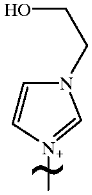 | 29 | 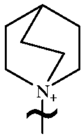 |
| 30 | 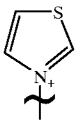 | 31 | 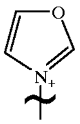 | 32 | 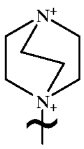 |
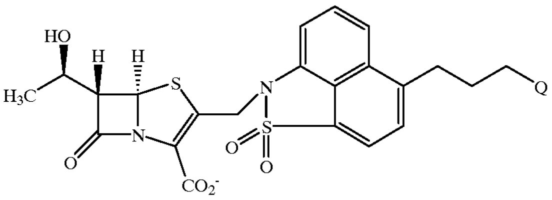

TABLE 5
| # | Q | # | Q | # | Q |
| --- | --- | --- | --- | --- | --- |
| 34 | 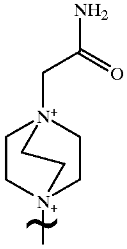 $L^-$ | 35 | 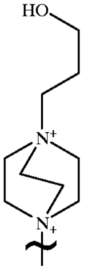 $L^-$ | 36 | 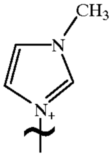 |
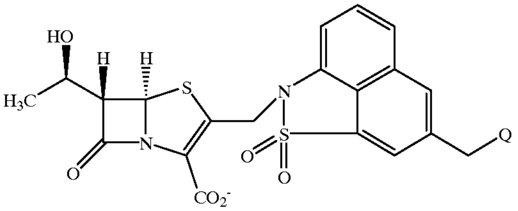
$L^-$
TABLE 6
| # | Q | # | Q | # | Q |
| --- | --- | --- | --- | --- | --- |
| 38 | 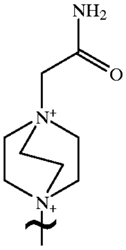 | 39 | 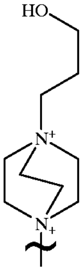 | 40 | 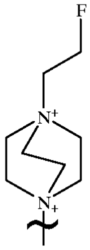 |
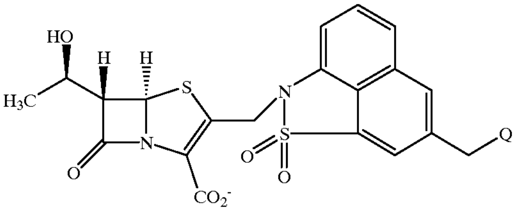
TABLE 7
| # | Q | # | Q | # | Q |
| --- | --- | --- | --- | --- | --- |
| 41 | 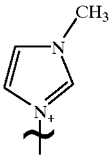 | 42 | 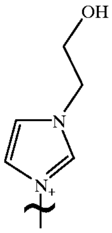 | 43 | 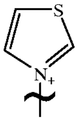 |
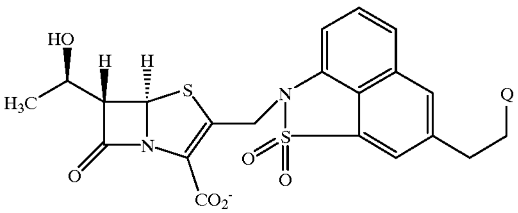

TABLE 8
| # | Q | # | Q | # | Q |
|---|---|---|---|---|---|
| 45 | 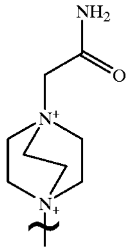 $L^-$ | 46 | 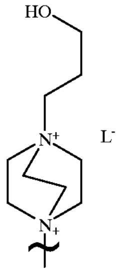 $L^-$ | 47 | 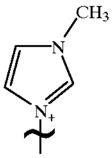 |
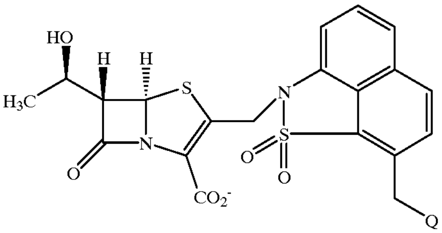
L-
TABLE 9
| # | Q | # | Q | # | Q |
|---|---|---|---|---|---|
| 49 | 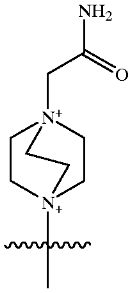 | 50 | 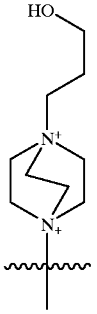 | 51 | 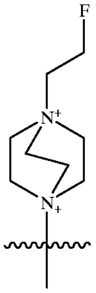 |
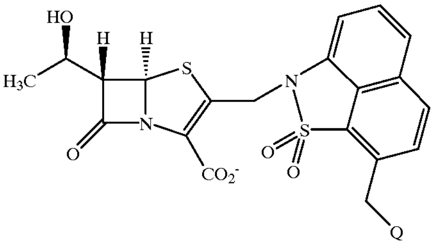
TABLE 10
| # | Q | # | Q | # | Q |
|---|---|---|---|---|---|
| 52 | 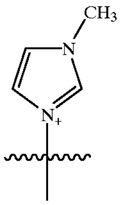 | 53 | 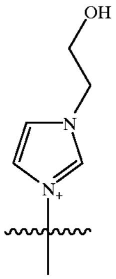 | 54 | 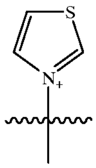 |
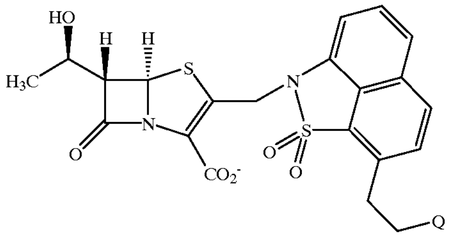

TABLE 11
| # | Q | # | Q | # | Q |
|---|---|---|---|---|---|
| 56 | 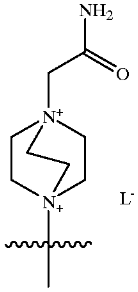 $L^-$ | 57 | 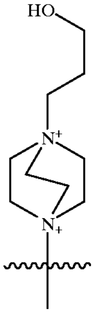 $L^-$ | 58 | 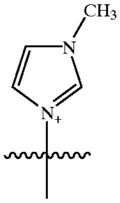 |
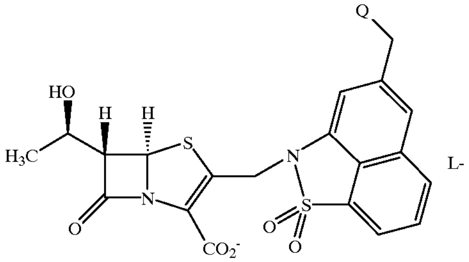
TABLE 12
| # | Q | # | Q | # | Q |
|---|---|---|---|---|---|
| 60 | 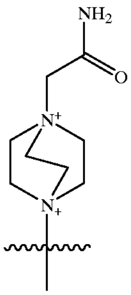 | 61 | 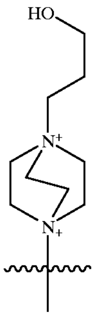 | 62 | 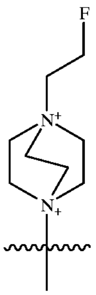 |
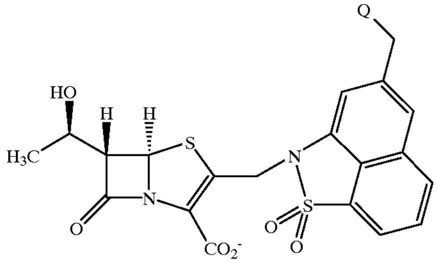
TABLE 13
| # | Q | # | Q | # | Q |
|---|---|---|---|---|---|
| 63 | 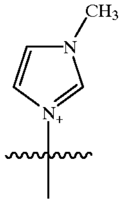 | 64 | 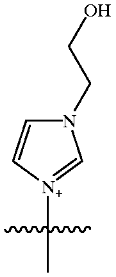 | 65 | 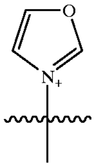 |
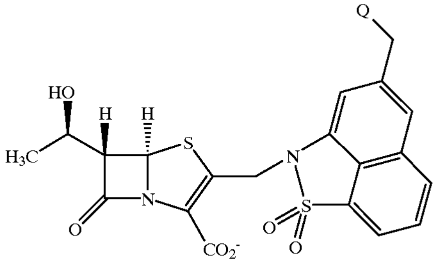
TABLE 14
| # | Q | # | Q | # | Q |
|---|---|---|---|---|---|
| 67 | 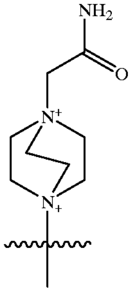 $L^-$ | 68 | 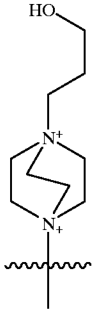 $L^-$ | 69 | 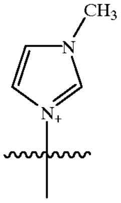 |
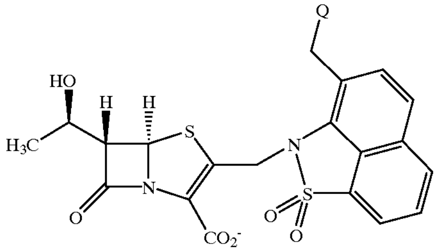

TABLE 15
| # | Q | # | Q | # | Q |
|---|---|---|---|---|---|
| 74 | 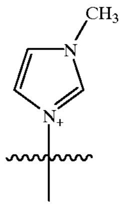 | 75 | 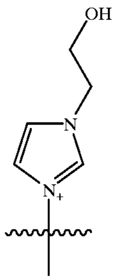 | 76 | 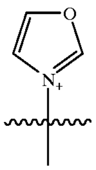 |
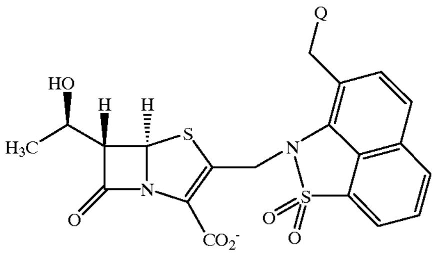
TABLE 16
| # | Q | # | Q | # | Q |
|---|---|---|---|---|---|
| 78 | 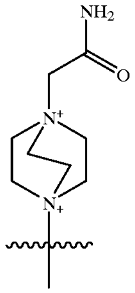 $L^-$ | 79 | 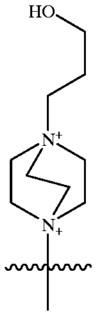 $L^-$ | 80 | 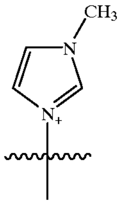 |
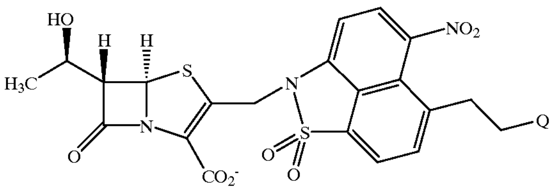
TABLE 17
| # | Q | # | Q | # | Q |
|---|---|---|---|---|---|
| 82 | 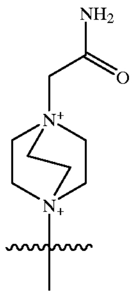 | 83 | 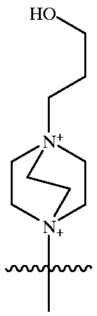 | 84 | 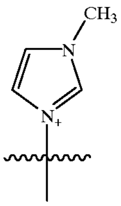 |
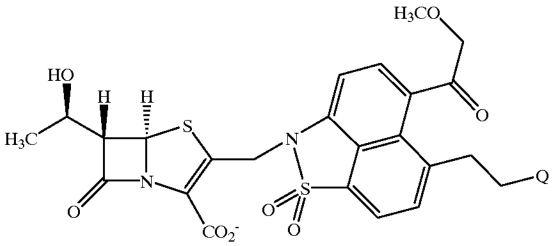
TABLE 18
| # | Q | # | Q | # | Q |
|---|---|---|---|---|---|
| 86 | 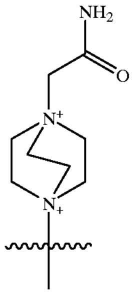 | 87 | 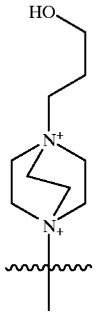 | 88 | 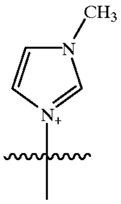 |
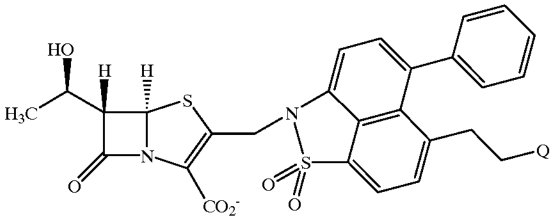

TABLE 19
| # | Q | # | Q | # | Q |
|---|---|---|---|---|---|
| 90 | 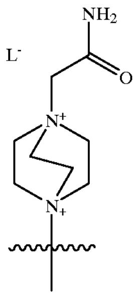 | 91 | 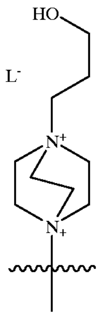 | 92 | 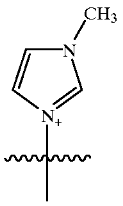 |
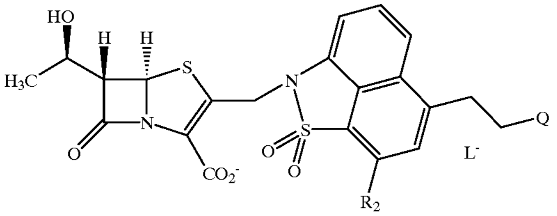
TABLE 20
| #93 | | #94 | | #95 | | #96 | |
|---|---|---|---|---|---|---|---|
| $R_2$ | Q | $R_2$ | Q | $R_2$ | Q | $R_2$ | Q |
| Cl | 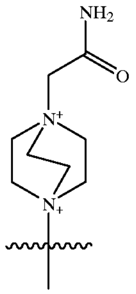 | $CH_3$ | 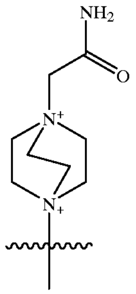 | Cl | 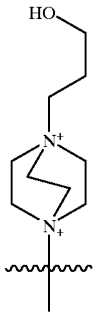 | $CH_3$ | 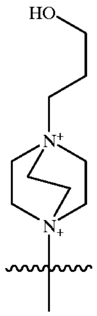 |
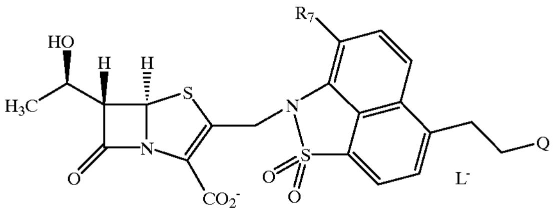

TABLE 21
| #97 | | #98 | | #99 | | #100 | |
|---|---|---|---|---|---|---|---|
| $R_7$ | Q | $R_7$ | Q | $R_7$ | Q | $R_7$ | Q |
| Cl | 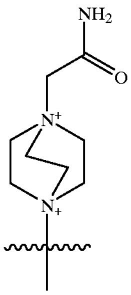 | $CH_3$ | 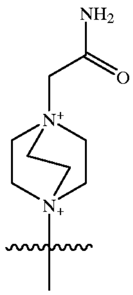 | Cl | 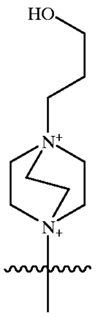 | $CH_3$ | 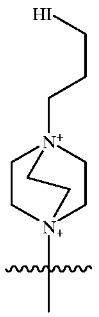 |
wherein Q is as defined in the tables and $L^-$ represents a pharmaceutically acceptable counterion.
The compounds of the present invention are prepared by two basic processes which are illustrated by the following generic schemes:
SYNTHESIS SCHEME I
NEUTRAL PENEMS
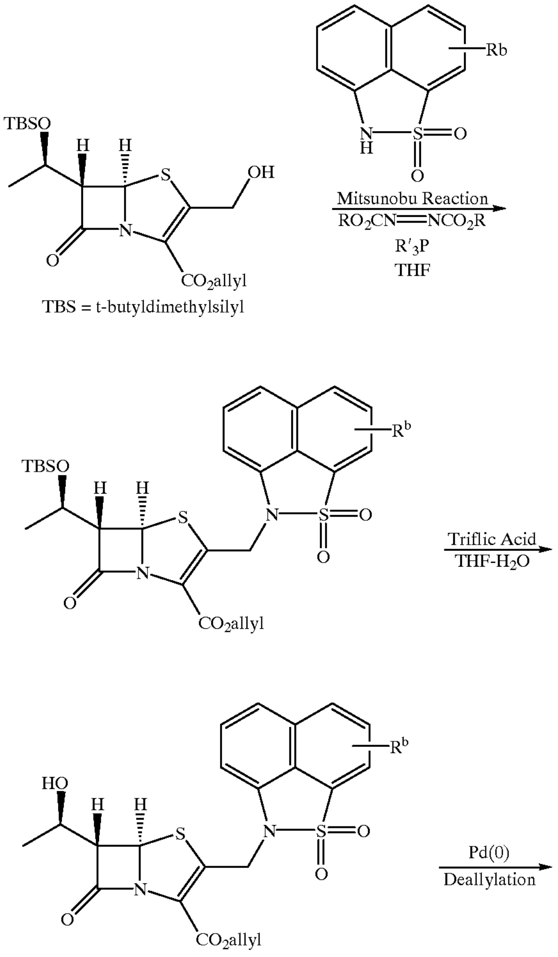
-continued
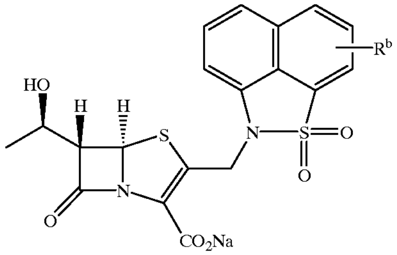
SYNTHESIS SCHEME II
CHARGED PENEMS
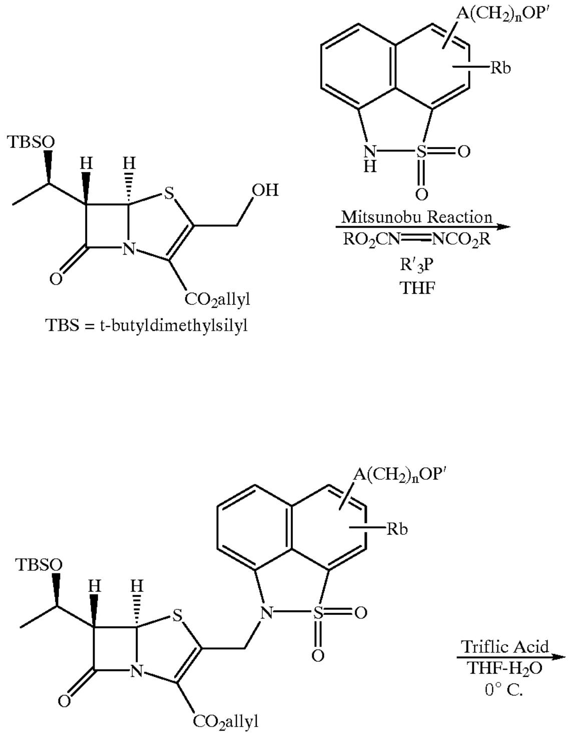

-continued

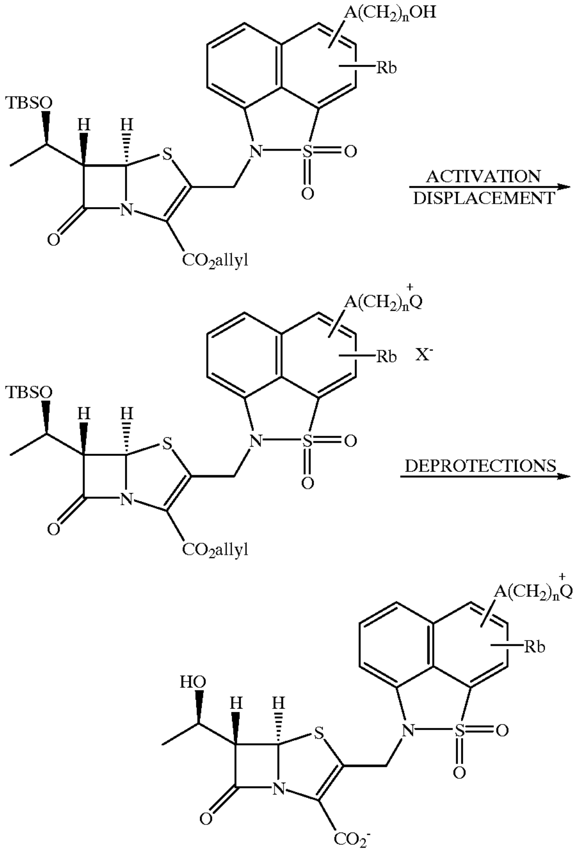

Many of compounds of the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of formula I in an amount effective to treat said infection.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many carbapenems are susceptible to attack by a renal enzyme known as dehydropeptidase (DHP). This attack or degradation may reduce the efficacy of the carbapenem antibacterial agent. Many of the compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (U.S. Pat. No. 0,007,614); and 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxymethylthio)-2-(2,2-dimethylcyclopropanecarboxamide)-2-heptenoic acid or a useful salt thereof.

The invention is further described in connection with the following non-limiting examples.

PREPARATIVE EXAMPLE 1

Synthesis of 5-(trimethylsilyloxymethyl)-1,8-naphthosultam

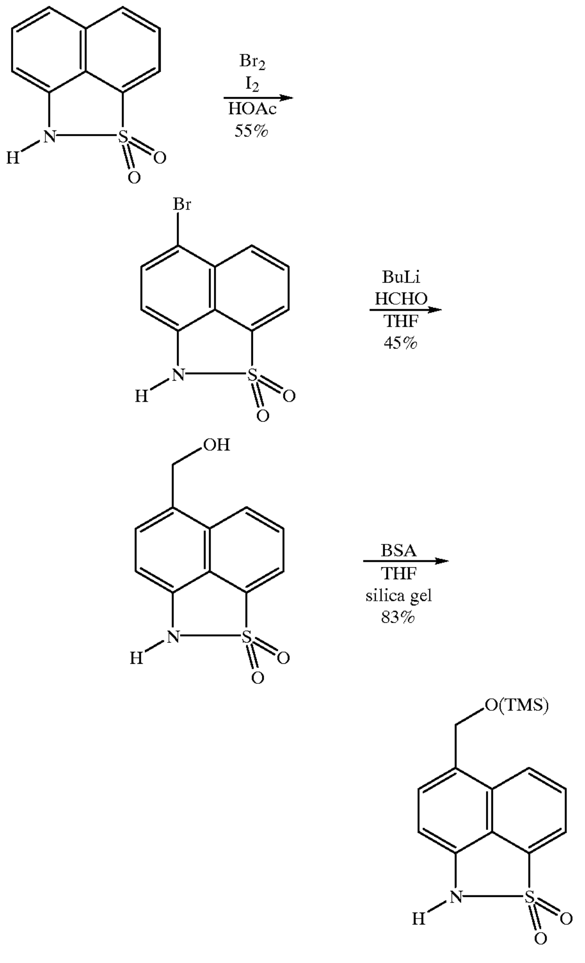

Step 1: 5-Bromo-1,8-naphthosultam

A suspension of 1,8-naphthosultam (5 g, 24.4 mmol) in acetic acid (20 mL) was treated with a dark solution of iodine (6.5 g, 25.6 mmol) and bromine (1.3 mL, 25.2 mmol) in acetic acid (20 mL) over 10 minutes. The suspension was stirred an additional 95 minutes then placed in a 60° C. oil bath for 30 minutes. After cooling to room temperature, the mixture was added to a 1% aqueous $NaHSO_3$ solution (300 mL). The dark precipitate was filtered and dried overnight under a stream of nitrogen. The resulting solid (6 g) was dissolved in ethyl acetate then silica gel (ca. 6 g) was added and the mixture was evaporated under vacuum. The silica-adsorbed mixture was loaded onto a 4.5×30 cm silica column (silica gel 60) and was eluted with 5% ethyl acetate/methylene chloride, collecting 25 mL fractions. Fractions 24–60 were combined and evaporated to give a green solid which was recrystallized from toluene to give the title compound as a light green solid (3.8 g).

$^1$H NMR ($CDCl_3$, 500 MHz) δ 6.82 (d, ArH), 6.83 (br.s, NH), 7.80 (d, ArH), 7.93 (t, ArH), 8.05 (d, ArH) and 8.38 (d, ArH).

Step 2: 5-(hydroxymethyl)-1,8-naphthosultam

A solution of 5-bromo-1,8-naphthosultam (0.5 g, 1.76 mmol) in anhydrous tetrahydrofuran (10 mL) under nitrogen was cooled in a dry ice/acetone bath in a three neck flask. N-butyllithium (2.75 mL of a 1.6 M solution in hexane, 4.4 mmol) was added over 2 minutes and the suspension was stirred an additional 7 minutes. Paraformaldehyde (0.317 g, 10.6 mmol), placed in the bulb of a drying tube which was attached to the flask, was heated with a heat gun while a slow stream of nitrogen was blown over the solid. The generated formaldehyde was carried into the flask and the carrier gas vented through a line connected to a Firestone valve over a period of 13 minutes. After an additional 5 minutes, the mixture was removed from the bath and stirred for 10 minutes. Aqueous hydrochloric acid (3 mL of a 2 N solution) was added and the clear suspension was stirred an additional 10 minutes. The mixture was partitioned between ethyl acetate (50 mL) and water (50 mL). The ethyl acetate layer was washed with saturated aqueous sodium chloride (20 mL), dried over magnesium sulfate, filtered, and evaporated. The solid residue (0.5 g) was dissolved in 5% methanol/methylene chloride and was loaded onto a 24×4.5 cm silica gel column (silica gel 60, packed/loaded/eluted with 5% methanol/methylene chloride), collecting 8 mL fractions. Fractions 12–42 were combined and evaporated to give the title compound as a white solid (0.185 g).

$^1$H NMR (DMSO-$d_6$, 500 MHz) δ 4.85 (d, $\underline{CH_2}OH$), 5.22 (t, $\underline{CH_2}OH$), 6.82 (d, ArH), 7.52 (d, ArH), 7.83 (t, ArH), 8.13 (d, ArH) and 8.38 (d, ArH).

Step 3: 5-(trimethylsilyloxymethyl)-1,8-naphthosultam

A solution of 5-(hydroxymethyl)-1,8-naphthosultam (0.185 g, 0.79 mmol) in tetrahydrofuran (1 mL) was treated with N,O-Bis(trimethylsilyl)acetamide ((BSA), 0.49 mL, 1.98 mmol). The mixture was stirred at room temperature for 1 hour then evaporated. The residual oil was dissolved in methylene chloride (1 mL) and was filtered through silica gel 60 (2.5 g), eluting the silica with additional methylene chloride (50 mL). The solvent was evaporated under vacuum and the residue was lyophilized from benzene (3 mL) to give the title compound as a white solid (0.20 g).

$^1$H NMR ($CDCl_3$, 500 MHz) δ 0.19 (s, $SiMe_3$), 5.07 (s, $CH_2$), 6.83 (d, ArH), 6.87 (br.s, NH), 7.50 (d, ArH), 7.78 (t, ArH), 7.95 (d, ArH) and 8.26 (d, ArH).

PREPARATIVE EXAMPLE 2

Synthesis of 5-(2-(trimethylsilyloxy)-ethyl)-1,8-naphthosultam

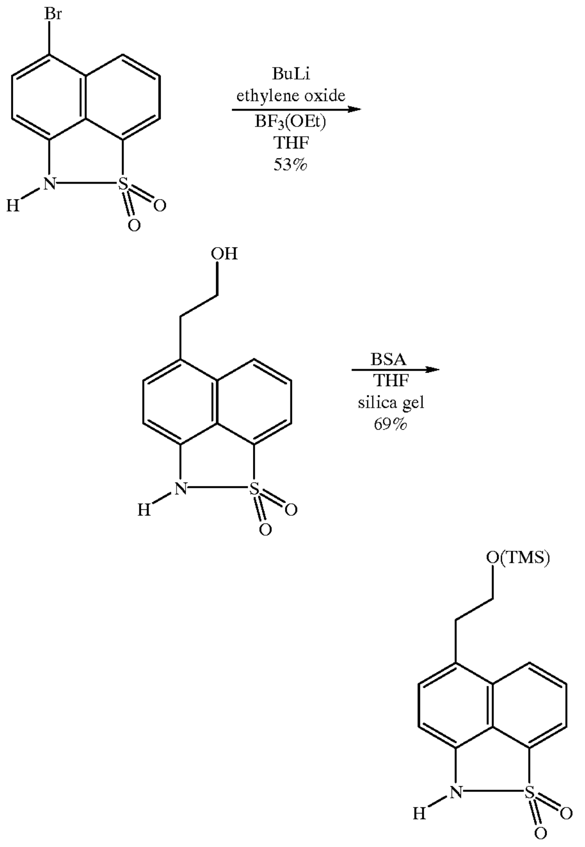

Step 1: 5-(2-(hydroxy)-ethyl)-1,8-naphthosultam

A solution of 5-bromo-1,8-naphthosultam (0.6 g, 2.11 mmol) in anhydrous tetrahydrofuran (10 mL) under nitrogen was cooled in a dry icel acetone bath. N-butyllithium (3.3 mL of a 1.6 M solution in hexane, 5.28 mmol) was added over 7 minutes and the suspension was stirred an additional 8 minutes. An excess of ethylene oxide was slowly bubbled into the mixture over 5 minutes. Boron trifluoride etherate (0.26 mL, 2.11 mmol) was then added over 5 minutes. After an additional 20 minutes, the reaction was quenched with the addition of acetic acid (0.35 mL, 6 mmol). The mixture was partitioned between ethyl acetate (100 mL) and water (100 mL). The ethyl acetate layer was washed with saturated aqueous sodium chloride (50 mL), dried over magnesium sulfate, filtered, and evaporated. The residual oil (0.7 g) was dissolved in 5% methanol/methylene chloride and was loaded onto a 24x2.75 cm silica gel column (silica gel 60, packed/loaded/eluted with 5% methanol/methylene chloride), collecting 8 mL fractions. Fractions 26–39 were combined and evaporated to give the title compound as an oil (0.28 g).

$^1$H NMR (DMSO-$d_6$, 500 MHz) δ 3.22 (t, $CH_2Ar$), 3.87 (t, $\underline{CH_2}OH$), 6.79 (d, ArH), 7.35 (d, ArH), 7.74 (t, ArH), 7.91 (d, ArH) and 8.21 (d, ArH).

Step 2: 5-(2-(trimethylsilyloxy)-ethyl)-1,8-naphthosultam

A solution of 5-(2-(hydroxy)-ethyl)-1,8-naphthosultam (0.09 g, 0.36 mmol) in tetrahydrofuran (1 mL) was treated with N,O-Bis(trimethylsilyl)acetamide (0.223 mL, 0.90 mmol). The mixture was stirred at room temperature for 20 minutes and was evaporated. The residual oil was dissolved in methylene chloride (3 mL) and was filtered through silica gel 60 (2.7 g), eluting the silica with additional methylene chloride (50 mL). The solvent was evaporated under vacuum and the residue was lyophilized from benzene (3 mL) to give the title compound as a white solid (0.08 g).

PREPARATIVE EXAMPLE 3

Synthesis of 4-(2-(trimethylsilyloxy)-ethyl)-1,8-naphthosultam

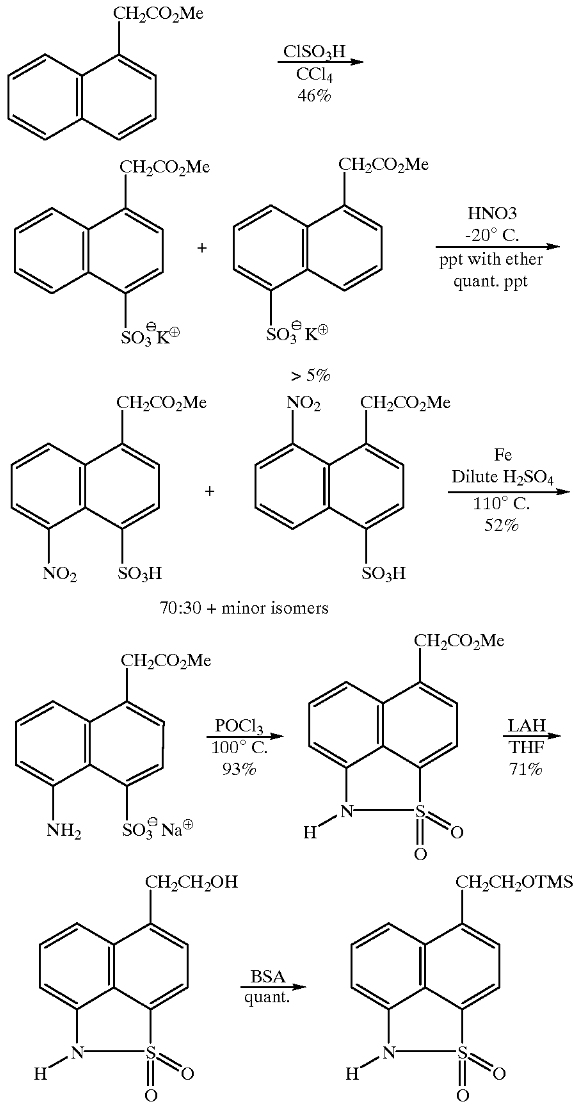

Step 1: potassium 1-(methoxycarbonylmethyl)-4-naphthalene sulfonate

A solution of methyl 1-naphthaleneacetate (1 mL, 5.77 mmol) in carbon tetrachloride (1 mL) was cooled under nitrogen in an ice bath. Chlorosulfonic acid (0.38 mL, 5.7 mmol) was added dropwise over 8 minutes. After an additional 30 minutes, the viscous mixture was removed from the bath and was stirred at room temperature for 17 hours to give a white solid. The solid was partitioned between methylene chloride (5 mL) and water (5 mL). After filtering through solka-floc, the methylene chloride layer was extracted with more water (2x5 mL), and the combined aqueous extracts were basified with potassium carbonate to give a precipitate. The suspension was concentrated to approximately 5 mL and was cooled in an ice bath. The suspension was then filtered and the collected solid was washed with cold water (2 mL). The solid was dried under a stream of nitrogen to give the title compound as a white solid (0.84 g).

$^1$H NMR (DMSO-$d_6$, 500 MHz) δ 3.73 (s, OMe), 4.27 (s, $CH_2$Ar), 7.53 (d, ArH), 7.71 (t, ArH), 7.76 (t, ArH), 8.06 (d, ArH), 8.10 (d, ArH) and 8.73 (d, ArH).

Step 2: 1-(methoxycarbonylmethyl)-5-nitro-4-naphthalene sulfonic acid

Potassium 1-(methoxycarbonylmethyl)-4-naphthalene sulfonate (10 g, 31.4 mmol) was added portionwise over 30 minutes to 90% nitric acid, which was cooled in a methanol/ice bath to approximately −15° C. After 2 hours, the bath temperature had reached −10° C. and diethyl ether (200 mL) was added to the mixture. The precipitated solid was filtered, washed with ether (100 mL) and isopropanol (20 mL), and dried under a stream of nitrogen to give the title compound as an approximately 70:30 mixture of the 5- and 8-nitro isomers (approximately 12 g).

$^1$H NMR ($D_2O$, 500 MHz) δ 3.69 (s, OMe), 4.30 (s, $CH_2$Ar), 7.67 (t, ArH), 7.71 (d, ArH), 8.18 (d, ArH), 8.29 (d, ArH) and 8.33 (d, ArH).

Step 3: sodium 1-(methoxycarbonylmethyl)-5-amino-4-naphthalene sulfonate 1-(methoxycarbonylmethyl)-5-nitro-4-naphthalene sulfonic acid (2 g, 6.15 mmol) was dissolved in water (20 mL), containing 0.5 mL concentrated sulfuric acid, and was added dropwise over 5 minutes to a refluxing suspension of iron (4 g, 71.6 mmol) in water (100 mL). After refluxing for one hour, the dark mixture was cooled to room temperature, made basic with sodium carbonate, and concentrated to approximately 30 mL. The residual mixture was placed on a CG-161 amberchrom resin column (2.5×30 cm). The column was washed with water (200 mL), 10% $MeCN/H_2O$ (200 mL), and 25% $MeCN/H_2O$(400 mL), collecting 25 mL fractions. Fractions 21–28 were combined and evaporated to give the title compound as a dark solid (0.675 g).

$^1$H NMR ($D_2O$, 500 MHz) δ 3.64 (s, OMe), 4.18 (s, $CH_2$Ar), 7.04 (d, ArH), 7.38 (d, ArH), 7.41 (d, ArH), 7.45 (t, ArH) and 8.22 (d, ArH).

Step 4: 4-(methoxycarbonylmethyl)-1,8-naphthosultam

Sodium 1-(methoxycarbonylmethyl)-5-amino-4-naphthalene sulfonate (0.675 g, 2.13 mmol) was suspended in phosphorous oxychloride (10 g, 65.2 mmol) and was refluxed for 1 hour to give a thin suspension. The mixture was cooled to room temperature and was partitioned between ethyl acetate (100 mL) and water (100 mL). The water layer was extracted with ethyl acetate (50 mL) and the combined ethyl acetate layers were washed with saturated aqueous sodium chloride (100 mL), dried over magnesium sulfate, filtered and evaporated to give the title compound as a solid (0.55 g).

$^1$H NMR ($CDCl_3$, 500 MHz) δ 3.72 (s, OMe), 4.15 (s, $CH_2$Ar), 6.86 (br s, NH), 6.97 (d, ArH), 7.60 (t, ArH), 7.67 (d, ArH), 7.71 (d, ArH) and 7.95 (d, ArH).

Step 5: 4-(2-(hydroxy)-ethyl)-1,8-naphthosultam

A solution of 4-(methoxycarbonylmethyl)-1,8-naphthosultam (0.2 g, 0.72 mmol) in tetrahydrofuran (2 mL) was cooled under nitrogen in an ice bath. Lithium aluminum hydride (1.44 mL of a 1.0 M solution in THF, 1.44 mmol) was added over 1 minute to give a light yellow suspension. After 30 minutes, water was carefully added and the mixture was partitioned between ethyl acetate (30 mL) and 1N hydrochloric acid (10 mL). The aqueous layer was extracted with ethyl acetate (50 mL) and the combined ethyl acetate layers were washed with saturated aqueous sodium chloride (10 mL), dried over magnesium sulfate, filtered and evaporated. The residual solid (0.16 g) was purified by preparative thin layer chromatography (2×1000 micron silica gel plates, developed/eluted with 5% $MeOH/CH_2Cl_2$) to give the title compound as a solid (0.127 g).

$^1$H NMR (0.14 mL $CDCl_3$ and 0.01 mL $CD_3OD$, 500 MHz) δ 3.33 (t, $CH_2$Ar), 3.91 (t, $\underline{CH_2}$OH), 6.84 (d, ArH), 7.49 (dd, ArH), 7.59 (d, ArH), 7.59 (d, ArH) and 7.83 (d, ArH).

Step 6: 4-(2-(trimethylsilyloxy)-ethyl)-1,8-naphthosultam

N,O-Bistrimethylsilylacetamide (0.31 mL, 1.25 mmol) was added to a solution of 4-(2-(hydroxy)-ethyl)-1,8-naphthosultam (0.125 g, 0.50 mmol) in tetrahydrofuran (1 mL). After one hour the mixture was evaporated and the residue was dissolved in methylene chloride (2 mL) and filtered through silica gel (2.5 g). The silica gel was eluted with methylene chloride (50 mL), the solvent was evaporated and the residue was lyophilized from benzene (3 mL) to give the title compound as an oil (0.16 g, quant.).

$^1$H NMR ($CDCl_3$, 500 MHz) δ 0.035 (s, TMS), 3.37 (t, $CH_2$Ar), 3.94 (t, $\underline{CH_2}$O(TMS)), 6.95 (d, ArH), 7.56 (dd, ArH), 7.64 (d, ArH), 7.71 (d, ArH) and 7.92 (d, ArH).

PREPARATIVE EXAMPLE 4

Synthesis of 4-(trimethylsilyloxymethyl)-1,8-naphthosultam

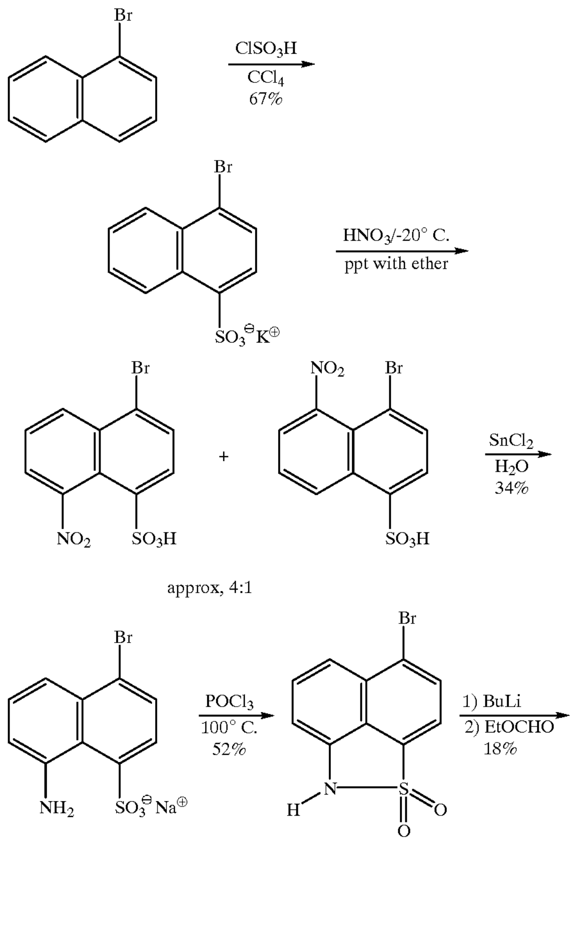

-continued

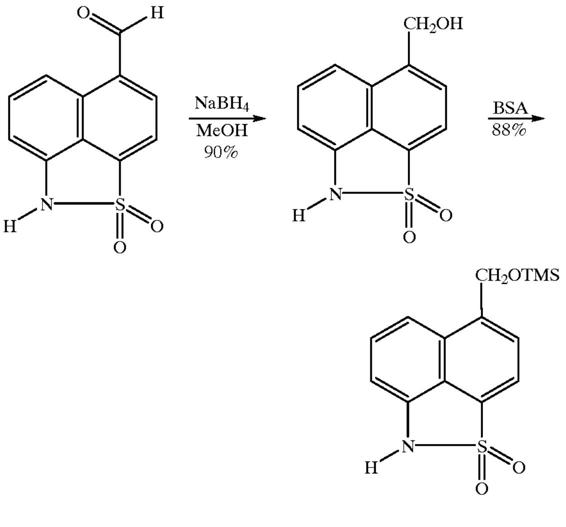

Step 1: potassium 1-bromo-4-naphthalenesulfonate

A solution of 1-bromonaphthalene (19 mL, 137 mmol) in carbon tetrachloride (24 mL) was cooled in an ice bath under nitrogen. Chlorosulfonic acid (9.1 mL, 137 mmol) was added dropwise over 20 minutes. After an additional 5 minutes, the heavy grey suspension was removed from the ice bath and was stirred at room temperature for 16 hours to give a grey paste. The mixture was partitioned between methylene chloride (100 mL) and water (300 mL). The aqueous layer was made basic with potassium carbonate and the resulting suspension was filtered. The collected solid was washed with methylene chloride (50 mL) and water (50 mL), and dried under vacuum to give the title compound as a white solid (30 g, 67%).

$^1$H NMR (DMSO-$d_6$, 500 MHz) δ 7.61 (m, ArH), 7.65 (m, ArH), 7.82 (m, 2ArH), 8.14 (dd, ArH), and 8.90 (dd, ArH).

Step 2: 1-bromo-5-nitro-4-naphthalene sulfonic acid

Potassium 1-bromo-4-naphthalenesulfonate (1.38 g, 4.24 mmol) was added portionwise over 20 minutes to 90% nitric acid (2 mL), which was cooled in a methanol/ice bath to approximately −15° C. After 1.5 hours, the mixture was placed in a refrigerator for 20 hours. Diethyl ether (20 mL) was added and the precipitated solid was filtered, washed with ether (100 mL) and isopropanol (20 mL), and dried under a stream of nitrogen to give the title compound as an approximately 4:1 mixture of the 5- and 8-nitro isomers (1.25 g).

$^1$H NMR ($D_2O$, 500 MHz) δ 7.70 (dd, ArH), 8.09 (d, ArH), 8.20 (d, ArH), 8.21 (dd, ArH), and 8.63 (d, ArH).

Step 3: sodium 1-bromo-5-amino-4-naphthalenesulfonate

1-Bromo-5-nitro-4-naphthalenesulfonate (1 g, 3.01 mmol) and tin chloride dihydrate (1.83 g, 8.1 mmol) were suspended in a mixture of water (10 mL) and ethanol (10 mL). The resulting mixture was heated for 3 hours in a 100° C. oil bath. The mixture was cooled to room temperature and filtered. The collected solid was suspended in water (20 mL) and the mixture was made basic with sodium carbonate then placed on a CG-161 amberchrom resin column (3×9 cm). The column was washed with water (300 mL) and was eluted with 25% $MeCN/H_2O$, collecting 12 mL fractions. Fractions 17–19 were combined and evaporated to give the title compound as a solid (0.33 g).

$^1$H NMR ($D_2O$, 500 MHz) δ 7.07 (dd, ArH), 7.49 (t, ArH), 7.83 (d, ArH), 7.85 (dd ArH) and 8.08 (d, ArH).

Step 4: 4-bromo-1,8-naphthosultam

Sodium 1-bromo-5-amino-4-naphthalenesulfonate (1.2 g, 3.70 mmol) was suspended in phosphorous oxychloride (10 mL, 107 mmol) and the mixture was refluxed for 1 hour to give a thin suspension. The mixture was cooled to room temperature and was added to ice (100 mL). The precipitate was collected and washed with water (20 mL) then dried under vacuum (0.675 g). A second crop was obtained from the filtrate (0.186 g). The combined solids were dissolved in 5% methanol in methylene chloride and were placed on a silica gel column (29×3.5 cm, packed and eluted with 5% methanol in methylene chloride), collecting 8 mL fractions. Fractions 27–39 were combined and evaporated to give the title compound as a solid (0.55 g).

$^1$H NMR (0.14 mL $CDCl_3$ and 0.01 mL $CD_3OD$, 500 MHz) δ 6.89 (d, ArH), 7.58(dd ArH), 7.68 (d, ArH), 7.73 (d, ArH) and 7.95 (d, ArH).

Step 5: 4-formyl-1,8-naphthosultam

A solution of 4-bromo-1,8-naphthosultam (0.24 g, 0.845 mmol) in anhydrous tetrahydrofuran (5 mL) was cooled in a dry ice/acetone bath under nitrogen. n-Butyllithium (1.32 mL of a 1.6 M solution in hexanes, 2.11 mmol) was added and the mixture was stirred for 5 minutes. Ethyl formate (1 mL, 12.4 mmol) was then added, and after an additional 5 minutes, 2N aqueous hydrochloric acid (3 mL) was added. The flask was removed from the bath and the yellow solution was partitioned between ethyl acetate (30 mL) and water (30 mL). The ethyl acetate layer was washed with saturated aqueous sodium chloride (20 mL), dried over magnesium sulfate, filtered, and evaporated. The residual oil was purified on preparative silica gel plates (3×1000 micron/developed and eluted with 5% methanol/methylene chloride) to give the title compound as a red solid (0.035 g).

$^1$H NMR ($CDCl_3$, 500 MHz) δ 7.09 (d, ArH), 7.78 (dd, ArH), 8.12 (d, ArH), 8.30(d, ArH), 8.70 (d, ArH) and 10.5 (s, CHO).

Step 6: 4-(hydroxymethyl)-1,8-naphthosultam

A solution of 4-formyl-1,8-naphthosultam (0.035 g, 0.15 mmol) in anhydrous methanol (1 mL) was cooled in an ice bath under nitrogen. Sodium borohydride (0.011 g, 0.3 mmol) was added and the solution was stirred for 30 minutes. The mixture was partitioned between methylene chloride (10 mL) and 0.2N aqueous hydrochloric acid (10 mL). The aqueous layer was extracted with 5% methanol in methylene chloride (2×10 mL), and the combined organic layers were evaporated to give the title compound as a yellow solid (0.032 g).

$^1$H NMR (0.14 mL $CDCl_3$ and 0.01 mL $CD_3OD$, 500 MHz) δ 5.13 (s, $\underline{CH_2}OH$), 6.85 (d, ArH), 7.50 (dd, ArH), 7.57 (d, ArH), 7.82 (d, ArH) and 7.88 (d, ArH).

Step 7: 4-(trimethylsilyloxymethyl)-1,8-naphthosultam

A solution of 4-(hydroxymethyl)-1,8-naphthosultam (0.032 g, 0.136 mmol) in tetrahydrofuran (0.5 mL) was treated with N,O-Bis(trimethylsilyl)acetamide (0.084 mL, 0.34 mmol). The mixture was stirred at room temperature for 45 minutes and was evaporated. The residual oil was dissolved in methylene chloride (1 mL) and was filtered through silica gel 60 (1 g), eluting the silica with additional methylene chloride (50 mL). The solvent was evaporated under vacuum and the residue was lyophilized from benzene (3 mL) to give the title compound as a white solid (0.037 g).

$^1$H NMR ($CDCl_3$, 500 MHz) δ 0.23 (s, $SiMe_3$), 6.78 (brs, NH), 5.23 (s, $CH_2$), 6.97 (d, ArH), 7.58 (dd, ArH), 7.64 (d, ArH), 7.90 (d, ArH) and 7.97 (d, ArH).

PREPARATIVE EXAMPLE 5

Synthesis of 4-(3-trimethylsilyloxyprop-1-yl)-1,8-naphthosultam

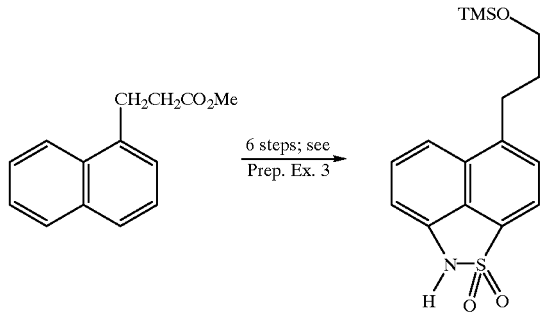

Steps 1–6 Synthesis of 4-(3-trimethylsilyloxyprop-1-yl)-1,8-naphthosultam

By substitution of methyl 1-naphthalenepropionate for methyl 1-naphthaleneacetate in the procedure of Preparative Example 3, 4-(3-trimethylsilyloxyprop-1-yl)-1,8-naphthosultam is prepared.

EXAMPLE 1

1

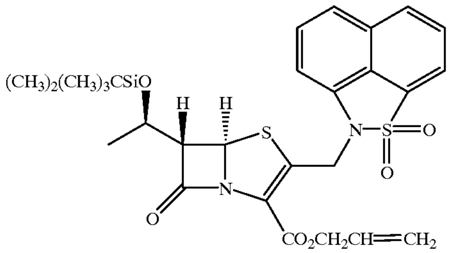

To a stirred solution of a mixture of penem carbinol (103.6 mg, 0.259 mmol)[prepared according to Corraz, A. J., et al, *J. Med. Chem.* 1992, 35, 1828], 1,8-naphthosultam (66.5 mg, 0.324 mmol) and triphenylphosphine (102.0 mg, 0.389 mmol) in 2 mL dry THF cooled to 0° C. was added diisopropylazodicarboxylate [DIAD] (77 $\mu$L, 0.389 mmol). The solution was stirred at 0° C. for 25 minutes, taken up in ethyl acetate, evaporated, and dried briefly in vacuo. The residue was then dissolved in methylene chloride and purified by plate layer chromatography (PLC), 2x2000$\mu$ [1 development, methylene chloride-ethyl acetate (50:1)]. The usual extractive filtration with ethyl acetate gave after evaporation and drying in vacuo 137.0 mg (90.1%) of a 3:1 mixture of penem 1 and its C-3 isomer, the SN2'product.

$^1$H NMR ($CDCl_3$) δ: 0.04 (s, 3H), 0.05 (s, 3H), 0.85 (s,9H), 1.14 (d, J=6.2 Hz, 3H), 3.69 (dd, J=1.7, 4.2 Hz, 1H), 4.21 (m,1H), 5.12 (d, J=18.4 Hz, 1H), 5.37 (d, J=18.4 Hz, 1H), 5.58 (d, J=1.7 Hz, 1H), and 6.81–8.09 (m,6H).

EXAMPLE 2

2

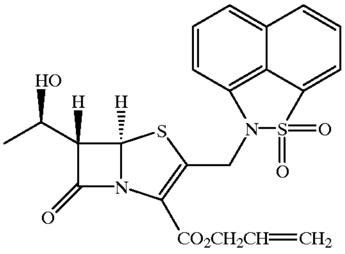

To a stirred solution of 124.9 mg (0.213 mmol) of the penem mixture prepared in Example 1 in 2 mL dry THF at 0° C. was added sequentially neat acetic acid (122 $\mu$L, 2.13 mmol) and then a solution of tetrabutylammonium fluoride (639 $\mu$L, 0.639 mmol) in THF. The mixture was stirred at 0° C. for 18 minutes and then at ambient temperature for 23 hours. The solution was then taken up in ethyl acetate and partitioned between ice, brine, and sodium bicarbonate. The organic phase was separated and washed again with brine. It was dried over anhydrous sodium sulfate, filtered, evaporated, and dried in vacuo. The residue was dissolved in methylene chloride and purified by PLC, 1x2000$\mu$ [1 development, methylene chloride-ethyl acetate (2:1)] to give 49.8 mg of impure product which was repurified by PLC, 2x1000$\mu$ [3 developments, methylene chloride-ethyl acetate (10:1)] to yield 20.0 mg of pure penem 2.

$^1$H NMR ($CDCl_3$) δ: 1.27 (d, J=6.3 Hz, 3H), 3.73 (dd, J=1.6, 5.8 Hz, 1H), 4.21 (m,1H), 5.11 (d, J=18.4 Hz, 1H), 5.43 (d, J=18.4 Hz, 1H), 5.59 (d, J=1.6 Hz, 1H), and 6.77–8.11 (m,6H).

EXAMPLE 3

3

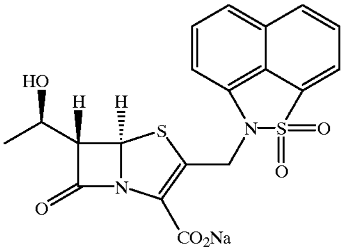

To a stirred solution of 20.0 mg (0.0423 mmol) of penem, prepared in the previous example, in 0.5 mL ethyl acetate and 0.5 mL methylene chloride at 0° C. was added 93 $\mu$L (0.0465 mmol) of a solution of 0.5M sodium-2-ethylhexanoate in ethyl acetate, followed by 4.9 mg (0.00423 mmol) of tetrakis(triphenylphosphine)palladium (0) and triphenylphosphine (3.3 mg, 0.0127 mmol). The mixture was stirred for 17 minutes and 7.5 mL of ether was added with stirring. The separated product was isolated by centrifugation and and it was purified by reverse phase plate layer chromatography (RP-PLC), 1x1000$\mu$ [1 development, water-acetonitrile (4:1)] in the cold. After extraction with acetonitrile-water (4:1), evaporation, and lyophilization 11.6 mg (60%) of penem 3 was obtained.

IR(nujol) 1763 and 1590 $cm^{-1}$; UV (water) $\lambda_{max}$ 241, 312 nm; $^1$H-NMR($D_2O$) δ: 1.45 (d, J=6.5 Hz, 3H), 3.98 (dd, J=1.2, 5.5 Hz, 1H), 4.4 (m,1H), 5.49 (d, J=16.4 Hz, 1H), 5.74 (d, J=16.4 Hz, 1H), 5.78 (d, J=1.2 Hz, 1H), and 7.3–8.55 (m,6H).

EXAMPLE 4

4

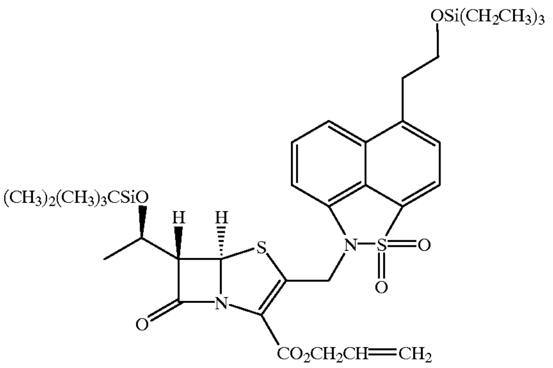

To a stirred solution of penem carbinol (59.0 mg, 0.148 mmol) in 2 mL dry THF was added 4-(2-triethylsilyloxyethyl)-1,8-naphthosultam (67.3 mg, 0.185 mmol) and triphenylphosphine (58.2 mg, 0.222 mmol). To this stirred mixture at 0° C. was added DIAD (44 μL, 0.185 mmol), and the solution was stirred at 0° C. for 37 minutes. It was taken up in ethyl acetate, evaporated, and dried in vacuo. The residue was dissolved in methylene chloride and purified by PLC, 2x1000μ [1 development, hexanes-ethyl acetate (4:1)] to give 118.6 mg (100%) of a mixture of the desired penem and the undesired C-3 isomer in a ratio of about 3:1 as determined by $^1$H-NMR.

$^1$H NMR ($CDCl_3$) δ: 0.04 (s, 3H), 0.05 (s, 3H), 0.52 (q, 6H), 0.86 (m,18H), 1.14 (d, J=6.3 Hz, 3H), 3.33 (t, J=6.8 Hz, 2H), 3.68 (dd, J=1.7, 4.2 Hz, 1H), 3.93 (t, J=6.8 Hz, 2H), 4.19 (m,1H), 5.11 (d, J=18.4 Hz, 1H), 5.36 (d, J=18.4 Hz, 1H), 5.56 (d, J=1.7 Hz, 1H), and 6.77–7.91 (m,5H).

EXAMPLE 5

5

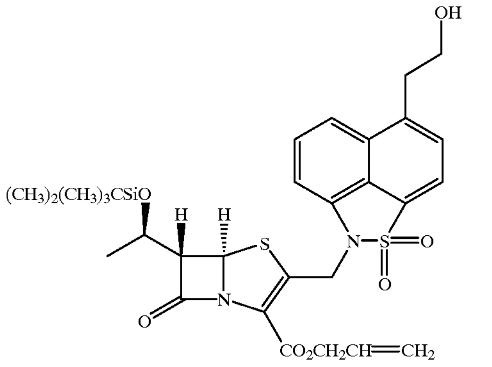

To a stirred solution of 50.0 mg (0.0671 mmol) of penem, prepared in the previous example, in 2 mL THF at 0° C. was added 200 μL water and 3 μL (0.0336 mmol) of triflic acid. The reaction was stirred at 0° C. for 35 minutes. It was taken up in ethyl acetate and partitioned between ice, brine, and sodium bicarbonate. The organic phase was separated and washed once with water and twice with brine. It was dried over anhydrous sodium sulfate, filtered, evaporated, and dried in vacuo to afford 42.1 mg (99.5%) of a mixture of penem 5 and its C-3 isomer in the same ratio as above.

$^1$H NMR ($CDCl_3$) δ: 0.04 (s, 3H), 0.05 (s, 3H), 0.86 (s,9H), 1.14 (d, 3H), 3.38 (t, 2H), 3.7 (dd, 1H), 4.0 (m, 2H), 4.2 (m,1H), 5.13 (d,1H), 5.36 (d, 1H), 5.56 (d, 1H), and 6.8–7.94 (m,5H).

EXAMPLE 6

6

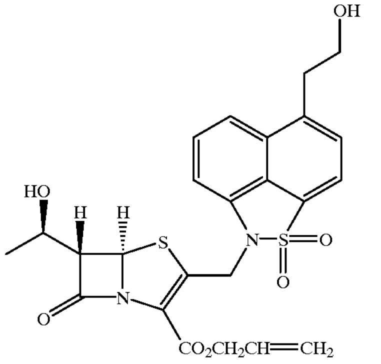

To a stirred solution of 116.9 mg (0.162 mmol) of penem, prepared in the previous example, in 2 mL THF at 0° C. was added 480 μL water, followed by triflic acid (14 μL, 0.0289 mmol). After 5 minutes, the ice-water bath was removed and the reaction mixture stirred for an additional 90.5 hours. The mixture was taken up in ethyl acetate and partitioned between ice, brine, and sodium bicarbonate. The organic phase was separated and washed again with brine. It was dried over anhydrous sodium sulfate, filtered, evaporated, and dried in vacuo. The residue was dissolved in methylene chloride and purified by PLC, 1x2000μ [1 development, methylene chloride-ethyl acetate (1:1)] to give 49.8 mg (59.6%) of a mixture of diol 6 and the C-3 isomer.

$^1$H NMR ($CDCl_3$) δ: 1.28 (d, 3H), 3.4 (t, 2H), 3.73 (dd, 1H), 4.03 (m, 2H), 4.22 (m,1H), 5.12 (d,1H), 5.35 (d, 1H), 5.59 (d, 1H), and 6.8–7.95 (m,5H).

EXAMPLE 7

7

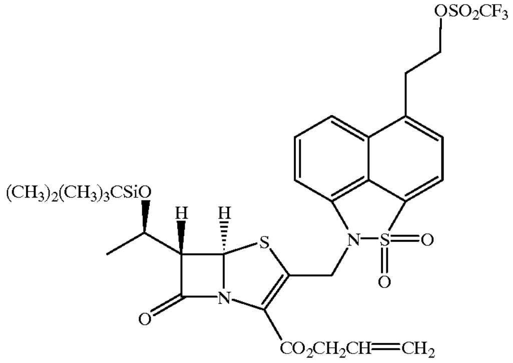

To a stirred solution of penem 5(58.5 mg, 0.0927 mmol), prepared in Example 5, in 1 mL sieve dried methylene chloride at ice-salt-water bath temperatures was added 2,6-lutidine (16 μl, 0.139 mmol) and triflic anhydride (20 μL, 0.116 mmol). The reaction mixture was stirred for 35 minutes and then an extra 8 μL of 2,6-lutidine and 10 μL of triflic anhydride was added. Stirring was continued at ice-salt-water bath temperatures for an additional 10 minutes. The mixture was taken up in ethyl acetate and partitioned between ice, brine, and 2N HCl. The organic phase was separated and washed again with brine. It was dried over anhydrous sodium sulfate, filtered, evaporated, and dried in vacuo to give 62.5 mg of crude triflate 7.

$^1$H NMR ($CDCl_3$) δ: 0.04 (s, 3H), 0.05 (s, 3H), 0.86 (s,9H), 1.15 (d, 3H), 3.65 (t, 2H), 3.69 (dd, 1H), 4.2 (m,1H), 4.7 (m, 2H), 5.15 (d,1H), 5.35 (d, 1H), 5.58 (d, 1H), and 6.86–7.98 (m,5H).

EXAMPLE 8

8

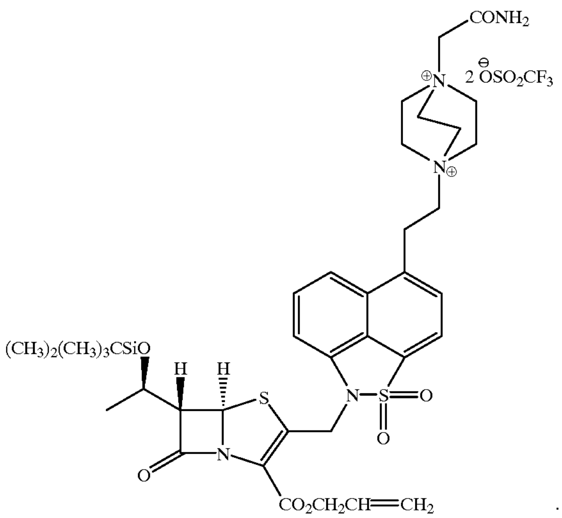

To a stirred solution of 62.5 mg (0.0819 mmol) of penem 7, prepared in the previous example, in 1 mL of sieve-dried acetonitrile at ambient temperature was added 26.2 mg (0.0819 mmol) of DABCO acetamide triflate. This was stirred further for 75 minutes and an extra 5.2 mg of DABCO acetamide salt was added. The reaction was stirred for an additional 1 hour and then taken up in ethyl acetate and evaporated and dried briefly in vacuo. Approximately 1 mL of acetone was added, followed by a large amount of anhydrous ethyl ether which caused the product to separate. The ether layer was decanted and the separated product was again washed with ether and it was dried in vacuo to afford 51.4 mg of penem 8.

$^1$H NMR (d-6 acetone) δ: 0.04 (s, 3H), 0.05 (s, 3H), 0.86 (s,9H), 1.12 (d, 3H), 3.5 (t, 2H), 3.85 (dd, 1H), 3.9 (t, 2H), 4.05 (m,1H), 4.3 (s,6H), 4.6 (s,6H), 4.68 (s, 2H), 5.25 (d,1H), 5.45 (d,1H), 5.62 (d,1H), and 7.1–8.15 (m,7H).

EXAMPLE 9

9

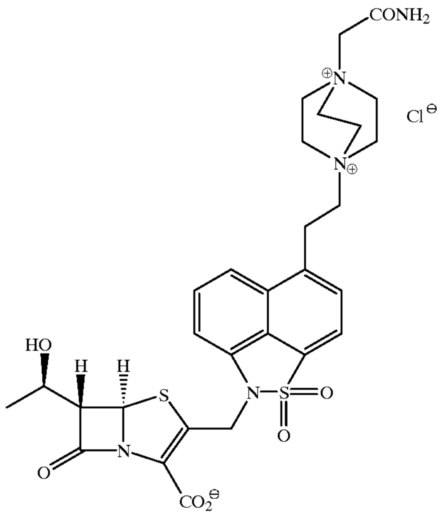

To a stirred solution of 48.2 mg (0.0445 mmol) of penem 8, prepared in the previous example, in 1 mL dry THF cooled to 0° C. was added 250 μL water and then 8 μL (0.0891 mmol) of triflic acid. The mixture was stirred at 0° C. for 5 min and then at ambient temperature for 93.5 hours. The reaction mixture was then cooled back to 0° C. and neutralized with 89 μL 0.5M aqueous $Na_2CO_3$. It was then taken up in acetone, evaporated, and dried in vacuo to afford 62.3 mg (100%) of crude desilylated penem intermediate, which was used immediately in the final deallylation step.

The penem product (43.1 mg, 0.0445 mmol) is dissolved in 1 mL sieve dried N,N-dimethylformamide (DMF) and cooled to 0° C. 2-Ethylhexanoic acid (7 μL, 0.0490 mmol) is added, followed by 98 μL (0.049 mmol) of a 0.5M solution of sodium-2-ethylhexanoate in ethylacetate, tetrakis (triphenylphosphine)palladium(0) (5.1 mg, 0.00445 mmol) and triphenyl-phosphine (11.7 mg, 0.0134 mmol). The solution is stirred at 0° C. for 30 minutes and is then triturated with a large amount of anhydrous ethyl ether and centrifuged. The ether layer is decanted and the process repeated. The product is dried and purified by conventional techniques to provide the penem final product 9.

EXAMPLE 10

10

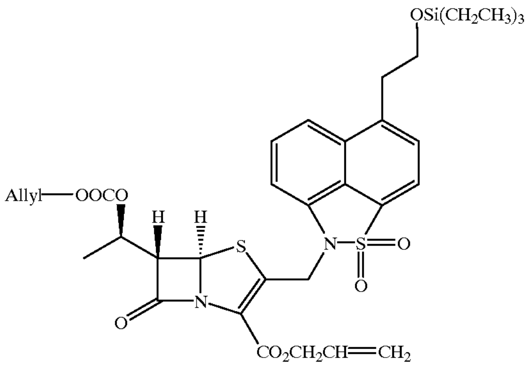

Using the procedure described in Example 4 and substituting the allyloxycarbonyl protected penem carbinol, the penem 10 is prepared.

EXAMPLE 11

11

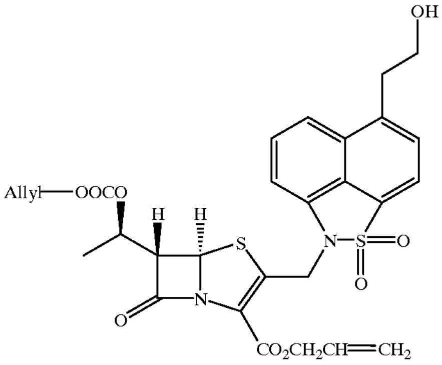

Following the procedure outlined in Example 5, the penem derivative prepared in the previous example is converted to penem 11.

EXAMPLE 12

12

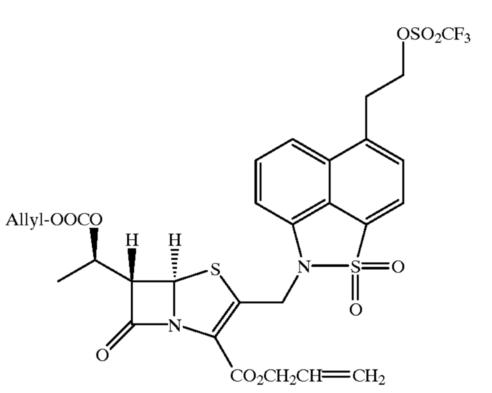

Following the procedure outlined in Example 6, the penem derivative prepared in the previous example is converted to penem 12.

EXAMPLE 13

13

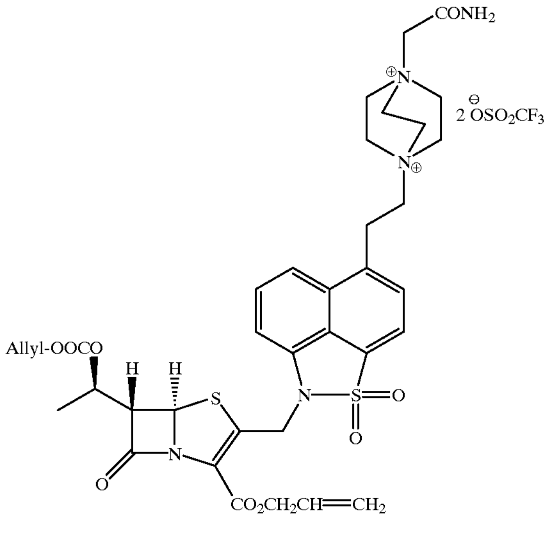

Following the procedure outlined in Example 8, the penem derivative prepared in the previous example is converted to penem 13.

EXAMPLE 14

9

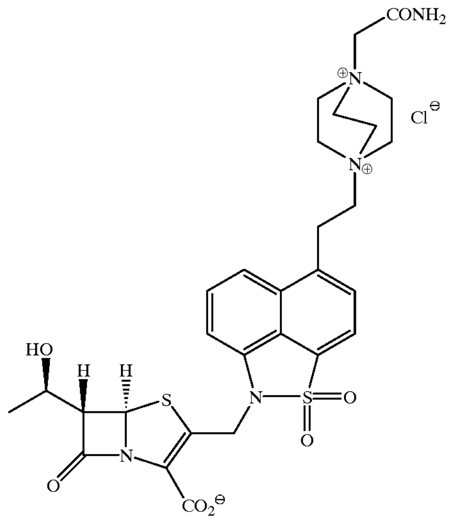

The simultaneous removal of the allyl protecting groups of penem 13, prepared in the previous example, is accomplished using the method of Jeffrey and McCombie, *J. Org. Chem.* 1982, 47, 587, and as described in Example 9, to provide penem 9.

What is claimed is:

1. A compound represented by formula I:

I

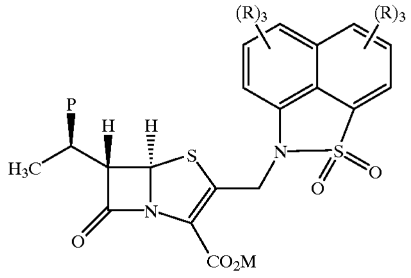

or a pharmaceutically acceptable salt thereof, wherein:

the molecule contains no more than two positive charges balanced by two negatively charged counterions consisting of $L^-$ and/or $CO_2M$, wherein $CO_2M$ is a carboxylate anion, to provide overall charge neutrality thereto;

$CO_2M$ represents a carboxylic acid, a carboxylate anion, balanced by a positively charged R group, or a cation, or a pharmaceutically acceptable ester group;

P represents hydrogen, hydroxyl or halo;

each R is independently selected from: —R*; A—$(CH_2)_n$—Q; —Q; hydrogen; halo; —CN; —$NO_2$; —$NR^aR^b$; —$OR^c$; —$SR^c$; —$C(O)NR^aR^b$; —C(O)$OR^h$; —$S(O)R^c$; —$SO_2R^c$; —$SO_2NR^aR^b$;

$—NR^aSO_2R^b$; $—C(O)R^a$; $—OC(O)R^a$; $—OC(O)NR^aR^b$; $—NR^aC(O)NR^bR^c$; $—NR^aCO_2R^h$; $—OCO_2R^h$; $—NR^aC(O)R^b$; $—C_{1-6}$ straight- or branched-chain alkyl, unsubstituted or substituted with one to four $R^d$ groups; and $—C_{3-7}$ cycloalkyl, unsubstituted or substituted with one to four $R^d$ groups;

A represents O, S or $CH_2$; n=0–3;

each $R^a$, $R^b$ and $R^c$ independently represents hydrogen, —R*, $—C_{1-6}$ straight- or branched-chain alkyl, unsubstituted or substituted with one to four $R^d$ groups, or $—C_{3-7}$ cycloalkyl, unsubstituted or substituted with one to four $R^d$ groups;

each $R^d$ independently represents halo; —CN; $—NO_2$; $—NR^eR^f$; $—OR^g$; $—SR^g$; $—CONR^eR^f$; $—COOR^g$; $—SOR^g$; $—SO_2R^g$; $—SO_2NR^eR^f$; $—NR^eSO_2R^f$; $—COR^e$; $—NR^eCOR^f$; $—OCOR^e$; $—OCONR^eR^f$; $—NR^eCONR^fR^g$; $—NR^eCO_2R^h$; $—OCO_2R^h$; $—C(NR^e)NR^fR^g$; $—NR^eC(NH)NR^fR^g$; $—NR^eC(NR^f)R^g$; —R* or —Q;

wherein when $—OR^g$ is OH, the OH group can be optionally protected by a hydroxyl protecting group;

$R^e$, $R^f$ and $R^g$ represent hydrogen; —R*; $—C_{1-6}$ straight- or branched-chain alkyl unsubstituted or substituted with one to four $R^i$ groups;

each $R^i$ independently represents halo; —CN; $—NO_2$; phenyl; $—NHSO_2R^h$; $—OR^h$, $—SR^h$; $—N(R^h)_2$; $—N^+(R^h)_3$; $—C(O)N(R^h)_2$; $—SO_2N(R^h)_2$; heteroaryl; heteroarylium; $—CO_2R^h$; $—C(O)R^h$; $—OCOR^h$; $—NHCOR^h$; guanidinyl; carbamimidoyl or ureido;

each $R^h$ independently represents hydrogen, a $—C_{1-6}$ straight or branched-chain alkyl group, a $—C_3–C_6$ cycloalkyl group or phenyl, or when two $R^h$ groups are present, Q is selected from the group consisting of:

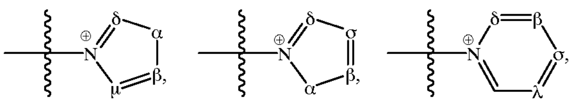

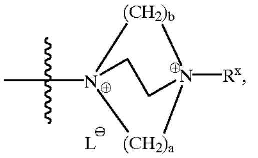

and

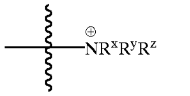

wherein:

a and b are 1, 2 or 3;

$L^-$ is a pharmaceutically acceptable counterion and can be present or absent as necessary to maintain the appropriate charge balance and represents a negative charge;

α represents O, S or $NR^s$;

β, δ, λ, μ and σ represent $CR^t$, N or $N^+R^s$, provided that no more than one of β, δ, λ, μ and σ is $N^+R^s$;

R* is selected from the group consisting of:

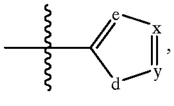,

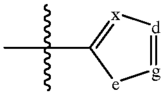

and

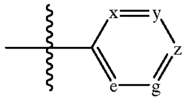

wherein:

d represents O, S or $NR^k$;

e, g, x, y and z represent $CR^m$, N or $N^+R^k$, provided that no more than one of e, g, x, y and z in any given structure represents $N^+R^k$;

$R^k$ represents hydrogen; $—C_{1-6}$ straight- or branched-chain alkyl, unsubstituted or substituted with one to four $R^i$ groups; or $—(CH_2)_nQ$ where n=1, 2 or 3 and Q is as previously defined;

each $R^m$ independently represents a member selected from the group consisting of: hydrogen; halo; —CN; $—NO_2$; $—NR^nR^o$; $—OR^n$; $—SR^n$; $—CONR^nR^o$; $—COOR^h$; $—SOR^n$; $—SO_2R^n$; $—SO_2NR^nR^o$; $—NR^nSO_2R^o$; $—COR^n$; $—NR^nCOR^o$; $—OCOR^n$; $—OCONR^nR^o$; $—NR^nCO_2R^h$; $—NR^nCONR^oR^h$; $—OCO_2R^h$; $—CNR^nNR^oR^h$; $—NR^nCNHNR^oR^h$; $—NR^nC(NR^o)R^h$; $—C_{1-6}$ straight- or branched-chain alkyl, unsubstituted or substituted with one to four $R^i$ groups; $—C_{3-7}$ cycloalkyl, unsubstituted or substituted with one to four $R^i$ groups; and $—(CH_2)_nQ$ where n and Q are as defined above;

$R^n$ and $R^o$ represent hydrogen, phenyl; $—C_{1-6}$ straight- or branched-chain alkyl unsubstituted or substituted with one to four $R^i$ groups;

each $R^s$ independently represents hydrogen; phenyl or $—C_{1-6}$ straight- or branched-chain alkyl, unsubstituted or substituted with one to four $R^i$ groups;

each $R^t$ independently represents hydrogen; halo; phenyl; —CN; $—NO_2$; $—NR^uR^v$; $—OR^u$; $—SR^u$; $—CONR^uR^v$; $—COOR^h$; $—SOR^u$; $—SO_2R^u$; $—SO_2NR^uR^v$; $—NR^uSO_2R^v$; $—COR^u$; $—NR^uCOR^v$; $—OCOR^u$; $—OCONR^uR^v$; $—NR^uCO_2R^v$; $—NR^uCONR^vR^w$; $—OCO_2R^v$; $—C_{1-6}$ straight- or branched-chain alkyl, unsubstituted or substituted with one to four $R^i$ groups;

$R^u$ and $R^v$ represent hydrogen or $—C_{1-6}$ straight- or branched-chain alkyl, unsubstituted or substituted with one to four $R^i$ groups;

each $R^w$ independently represents hydrogen; $—C_{1-6}$straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

$R^x$ represents hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, $—C(O)—R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteraryl, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups; and $R^y$ and $R^z$ represent hydrogen; phenyl; $—C_{1-6}$ straight or branched chain alkyl, unsubstituted or substituted with one to four $R^i$ groups, and optionally interrupted by O, S, $NR^w$, $N^+R^hR^w$ or —C(O)—.

2. A compound in accordance with claim 1 wherein $CO_2M$ represents a carboxylate anion.

3. A compound in accordance with claim 2 wherein M represents a negative charge which is balanced by a positively charged R group.

4. A method of treating or preventing a bacterial infection in a mammalian patient in need thereof, comprising administering to said patient an effective amount of a compound of claim 1.

5. A compound in accordance with claim 1 wherein one R represents a group which contains a positively charged moiety, and the remaining R groups are selected from hydrogen and $C_{1-6}$ straight or branched chain alkyl, unsubstituted or substituted with one to four $R^d$ groups.

6. A compound in accordance with claim 5 wherein one R represents a group containing a positively charged moiety and the remaining R groups are hydrogen.

7. A compound in accordance with claim 1 wherein the R groups contain from 1–2 positive charges.

8. A compound in accordance with claim 1 wherein one R group represents a —$C_{1-6}$ straight or branched chain alkyl group, substituted with one to four $R^d$ groups, wherein one Rd group represents —R* or Q.

9. A compound in accordance with claim 1 wherein Q is selected from the group consisting of:

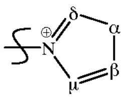,
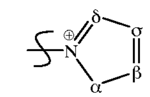
and
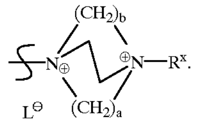

10. A compound in accordance with claim 9 wherein Q represents:

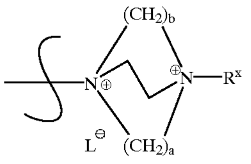

$L^-$, a and b are as originally defined, and $R^x$ represents a member selected from the group consisting of: hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups, and $R^h$, $R^i$, and $R^w$ are as originally defined.

11. A compound in accordance with claim 1 wherein Q represents —$N^+R^xR^yR^z$, wherein $R^x$, $R^y$ and $R^z$ are as originally defined.

12. A compound in accordance with claim 1 wherein one R* group is selected from:

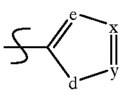
and
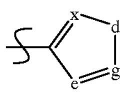

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

13. A compound in accordance with claim 1 wherein R is A—$(CH_2)_n$—Q, wherein A and Q are as originally defined.

14. A compound in accordance with claim 1 represented by formula Ia:

Ia

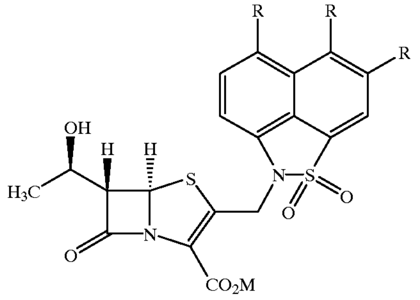

wherein:

$CO_2M$ represents a carboxylate anion;

one R group which is attached to the naphthosultam contains at least one positively charged moiety, and the remaining R groups are selected from hydrogen and $C_{1-6}$ straight or branched chain alkyl, unsubstituted or substituted with one to four $R^d$ groups;

$R^d$ is as originally defined;

$R^h$ represents hydrogen or a $C_{1-6}$ straight or branched chain alkyl group;

Q is selected from the group consisting of:

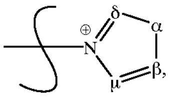
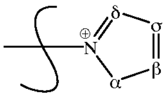
and
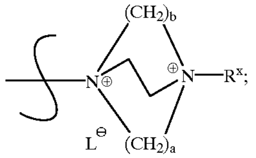

wherein $L^-$, a and b are as originally defined, and $R^x$ represents a member selected from the group consisting of: hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl or heteroaryl group being optionally substituted with from one to four $R^i$ groups or with one to two $C_{1-3}$ straight- or branched-chain alkyl groups, said alkyl groups being unsubstituted or substituted with one to four $R^i$ groups;

R* is selected from:

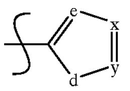
and
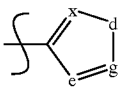

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

15. A compound in accordance with claim 1 represented by formula Ib:

Ib

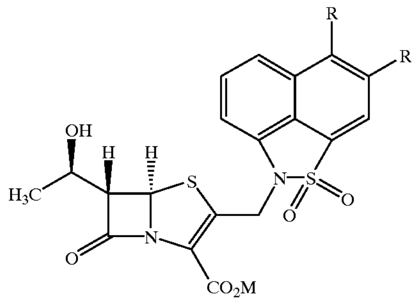

or a pharmaceutically acceptable salt thereof, wherein:

$CO_2M$ represents a carboxylate anion;

one R group is attached to the naphthosultam which contains a positively charged moiety, and the other R group is selected from hydrogen and $C_{1-6}$ straight or branched chain alkyl, unsubstituted or substituted with one to four $R^d$ groups;

$R^d$ is as originally defined;

Q is selected from the group consisting of:

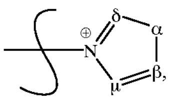 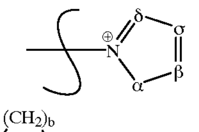 and

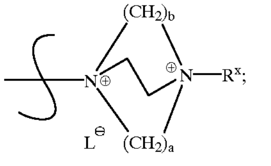

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight- or branched-chain alkyl groups, said alkyl groups being unsubstituted or substituted with one to four $R^i$ groups;

$R^h$ represents hydrogen or a $C_{1-6}$ straight or branched chain alkyl group;

$R^w$ is as originally defined;

R* is selected from:

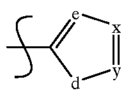 and 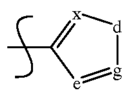

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

16. A compound in accordance with claim 1 represented by formula Ic:

Ic

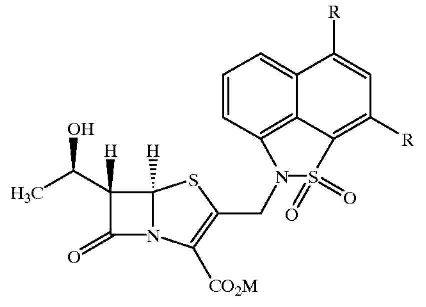

or a pharmaceutically acceptable salt thereof, wherein:

$CO_2M$ represents a carboxylate anion;

one R group is attached to the naphthosultam which contains a positively charged moiety, and the other R group is selected from hydrogen, halo and $C_{1-6}$ straight or branched chain alkyl, unsubstituted or substituted with one to four $R^d$ groups;

$R^d$ is as originally defined;

Q is selected from the group consisting of:

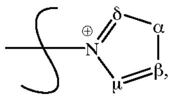 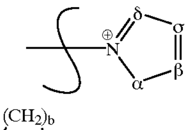 and

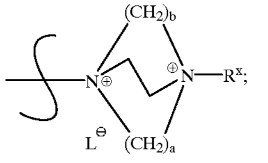

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

$R^h$ represents hydrogen or a $C_{1-6}$ straight or branched chain alkyl group;

$R^w$ is as originally defined;

R* is selected from:

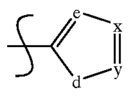 and 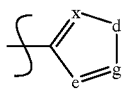

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

17. A compound in accordance represented by formula Id:

Id

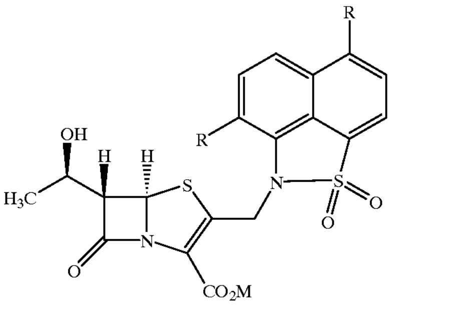

or a pharmaceutically acceptable salt thereof, wherein:

$CO_2M$ represents a carboxylate anion;

one R group is attached to the naphthosultam which contains a positively charged moiety, and the other R group is selected from hydrogen, halo and $C_{1-6}$ straight or branched chain alkyl, unsubstituted or substituted with one to four $R^d$ groups;

$R^d$ is as originally defined;

Q is selected from the group consisting of:

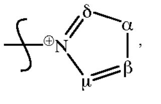 , 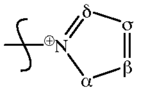 and 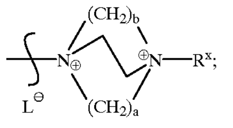

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight- or branched-chain alkyl groups, said alkyl groups being unsubstituted or substituted with one to four $R^i$ groups;

$R^h$ represents hydrogen or a $C_{1-6}$ straight or branched chain alkyl group;

$R^w$ is as originally defined;

R* is selected from:

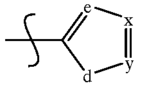 and 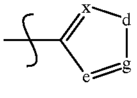 .

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

18. A compound in accordance with claim 1 represented by formula Ie:

Ie

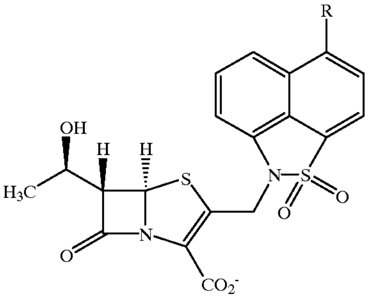

or a pharmaceutically acceptable salt thereof, wherein:

R contains a positively charged moiety selected from the group consisting of: —R*, Q, A—$(CH_2)_n$—Q, and a $C_{1-6}$ straight or branched alkyl chain substituted with one $R^d$ group, wherein A is as originally described;

$R^d$ is independently selected —R* or Q;

Q is selected from the group consisting of:

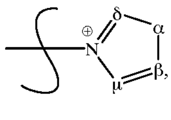 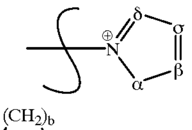 and

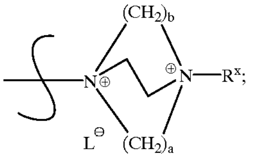

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

R* is selected from:

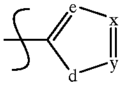 and 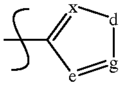

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

19. A compound in accordance with claim 1 represented by formula If:

If

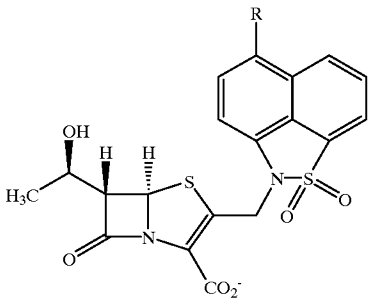

or a pharmaceutically acceptable salt thereof, wherein:

R contains a positively charged moiety selected from the group consisting of: —R*, Q, A—$(CH_2)_n$—Q, and a $C_{1-6}$ straight or branched alkyl chain substituted with one $R^d$ group, wherein A is as originally described;

$R^d$ is independently selected —R* or Q;

Q is selected from the group consisting of:

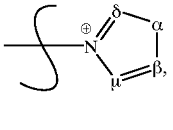
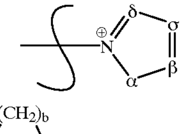
and
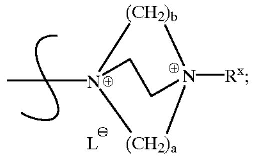

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

R* is selected from:

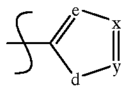
and
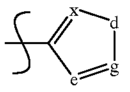

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

20. A compound in accordance with claim 19 wherein R represents

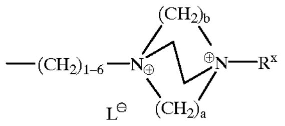

and $R^x$, a, b and $L^-$ are as originally defined.

21. A compound in accordance with claim 1 represented by formula Ig:

Ig

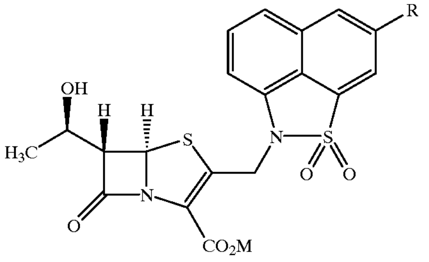

wherein: R represents

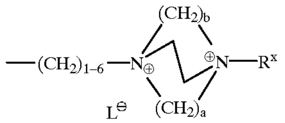

and $R^x$, a, b and $L^-$ are as originally defined.

22. A compound in accordance with claim 21 wherein R represents A—$(CH_2)_n$—Q, wherein A is $CH_2$ and Q is selected from the group consisting of:

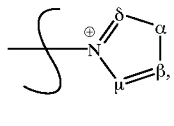
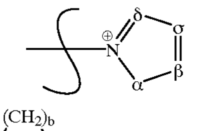
and
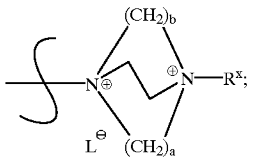

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups.

23. A compound represented by the formulas in Table 1:
A-2
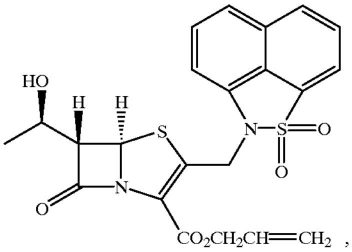
,
A-3
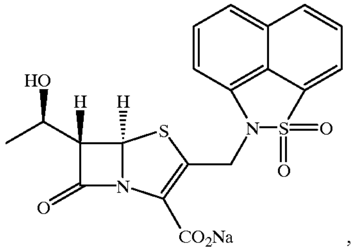
,
A-4
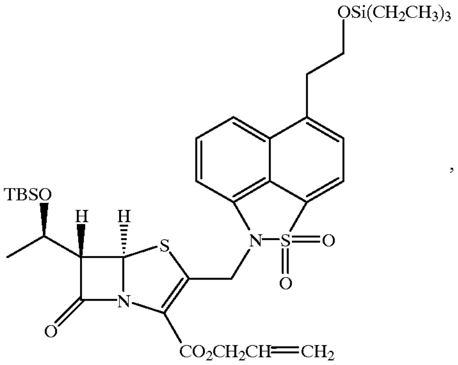
,
A-5
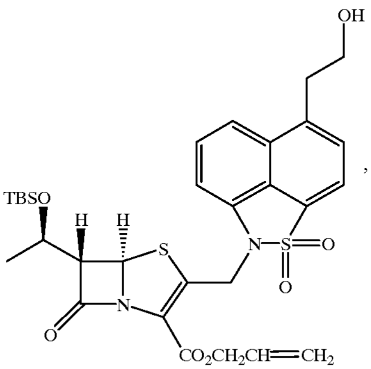
,
-continued
A-6
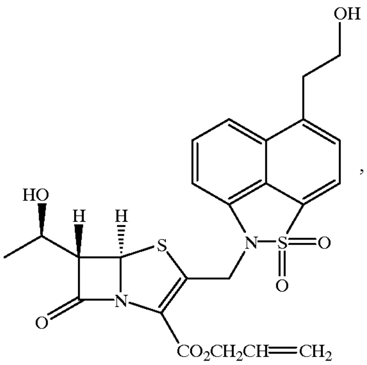
,
A-7
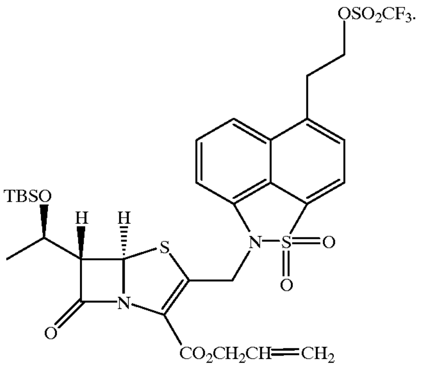
A-9
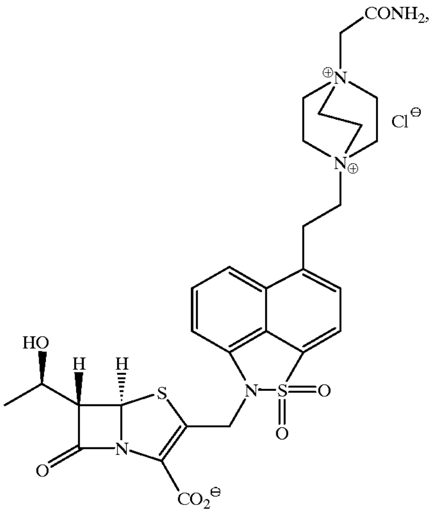

-continued
A-10
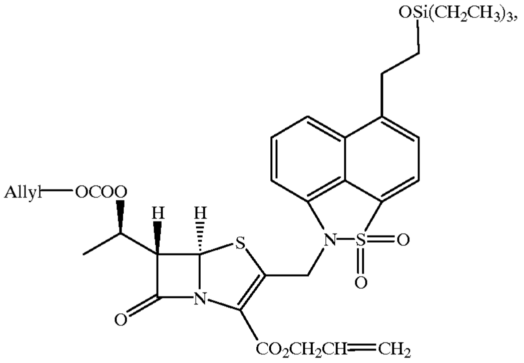
A-11
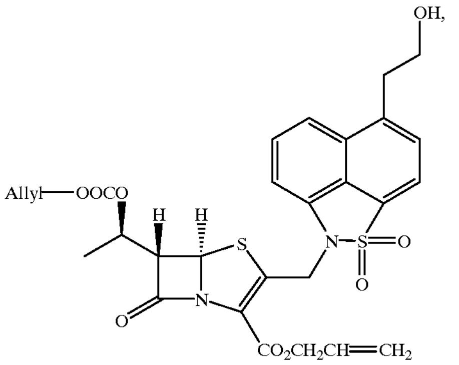
A-12
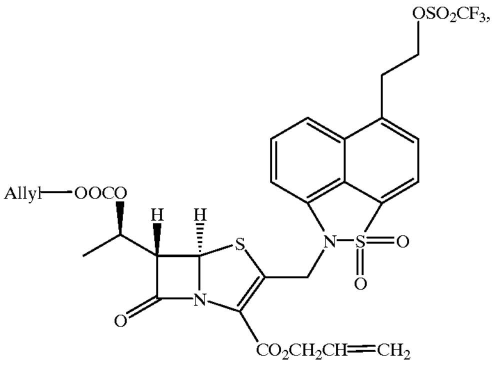
and
-continued
A-14
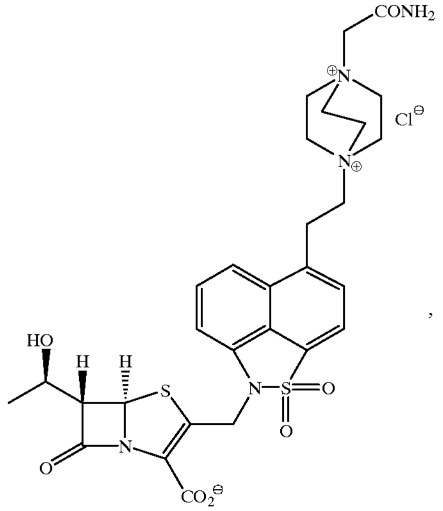
in which TBS denotes t-butyldimethylsilyl.
24. A compound in accordance with claim 1 represented by the formulas:
E-1
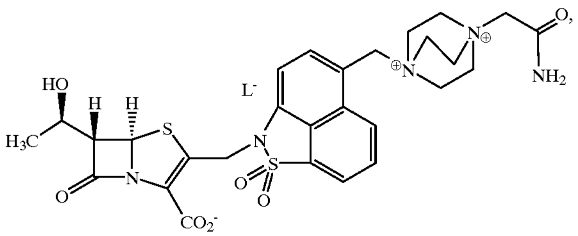
E-2
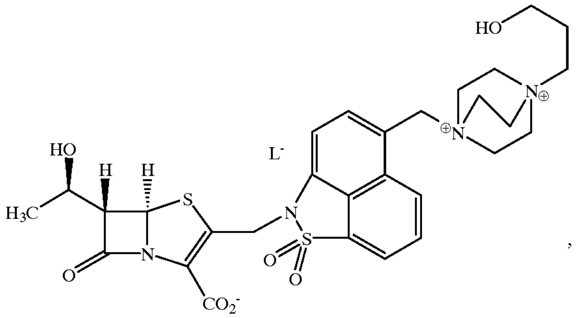
E-3
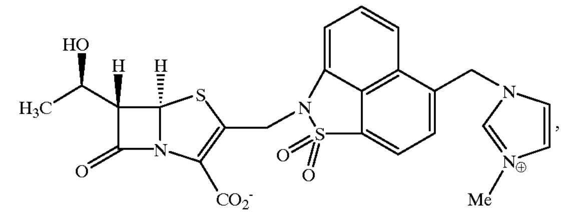

-continued
E-4
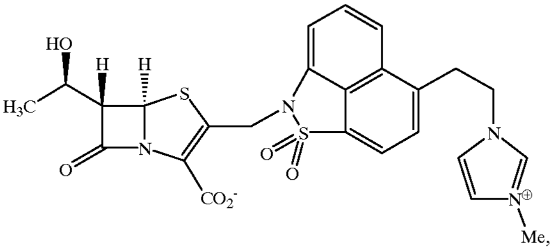
E-5
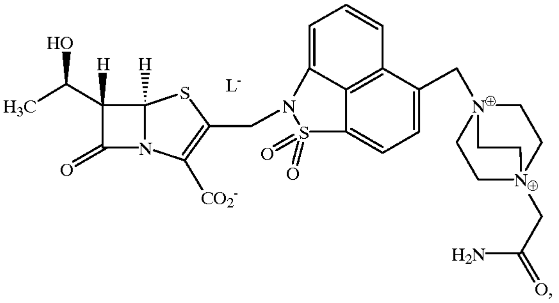
E-7
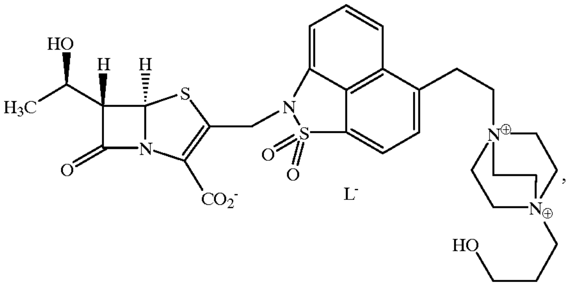
-continued
E-6
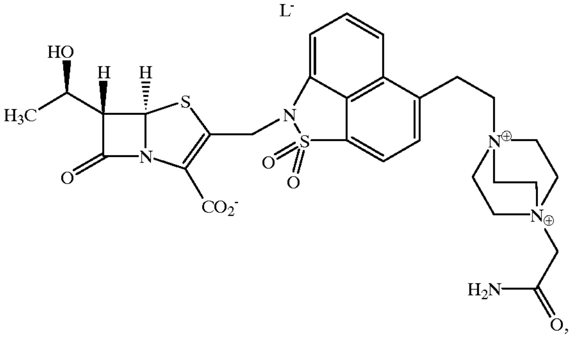
and
E-8
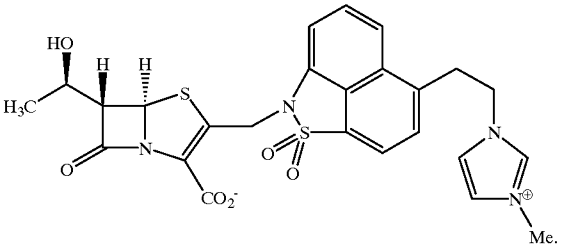
25. A compound in accordance with claim 1 falling within Tables 3–21:
TABLE 3
| # | Q | # | Q | # | Q |
|---|---|---|---|---|---|
| 9 | 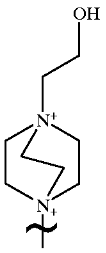 | 10 | 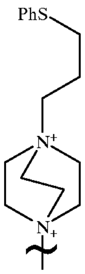 | 11 | 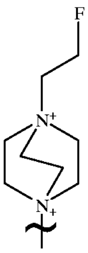 |
Ph = phenyl TABLE 3-continued
| # | Q | # | Q | # | Q |
|---|---|---|---|---|---|
| 12 | 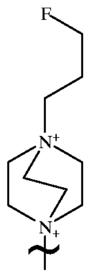 | 13 | 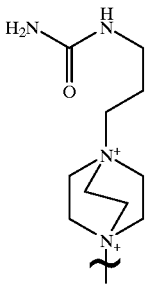 | 14 | 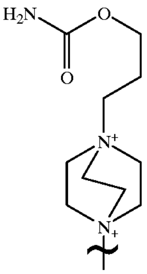 |
| 15 | 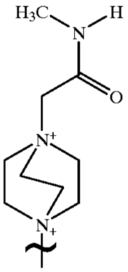 | 16 | 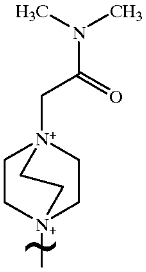 | 17 | 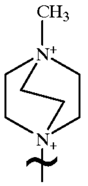 |
| 18 | 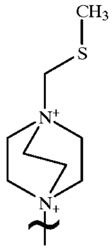 | 19 | 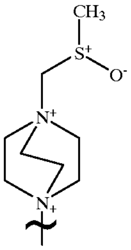 | 20 | 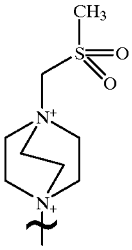 |
| 21 | 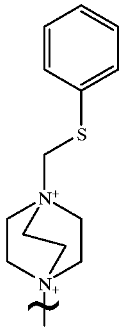 | 22 | 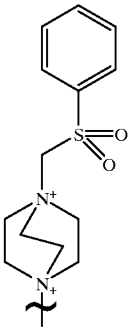 | 23 | 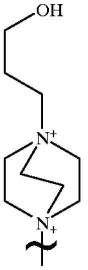 |

TABLE 3-continued
| # | Q | # | Q | # | Q |
|---|---|---|---|---|---|
| 24 | 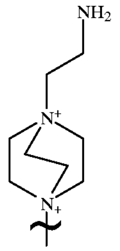 | 25 | 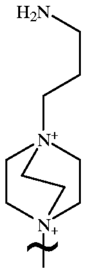 | 26 | 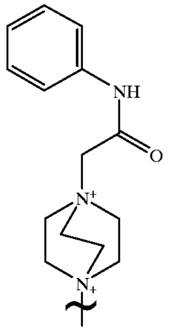 |
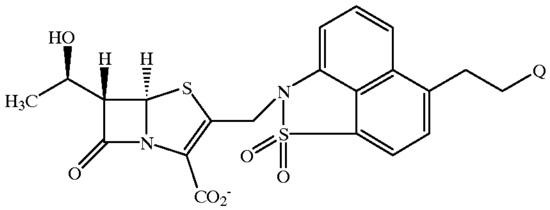
TABLE 4
| # | Q | # | Q | # | Q |
|---|---|---|---|---|---|
| 27 | 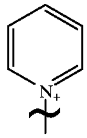 | 28 | 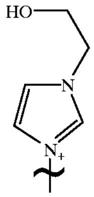 | 29 | 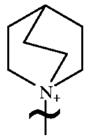 |
| 30 | 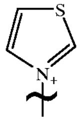 | 31 | 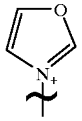 | 32 | 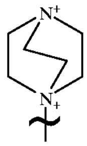 |
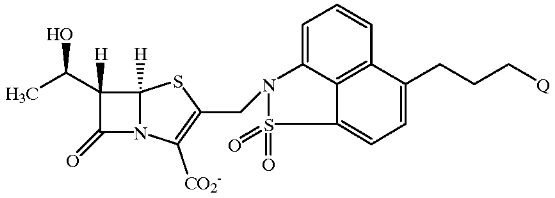

TABLE 5
| # | Q | # | Q | # | Q |
|---|---|---|---|---|---|
| 34 | 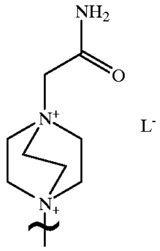 | 35 | 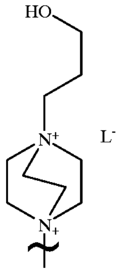 | 36 | 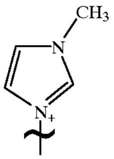 |
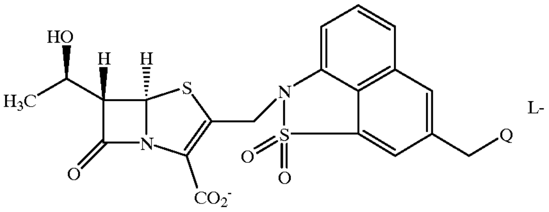
TABLE 6
| # | Q | # | Q | # | Q |
|---|---|---|---|---|---|
| 38 | 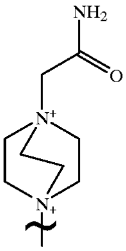 | 39 | 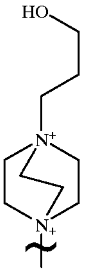 | 40 | 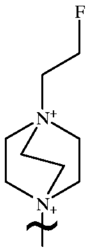 |
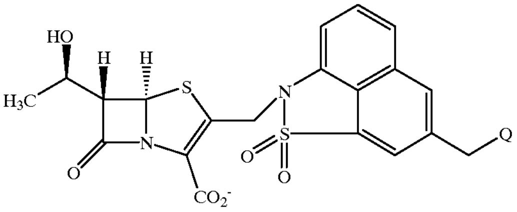
TABLE 7
| # | Q | # | Q | # | Q |
|---|---|---|---|---|---|
| 41 | 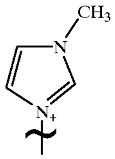 | 42 | 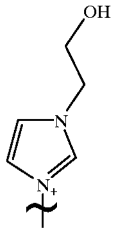 | 43 | 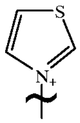 |
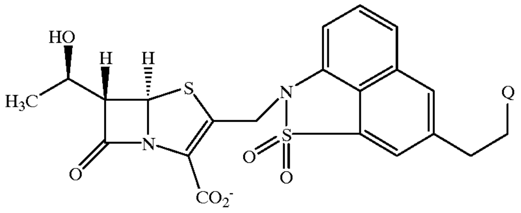

TABLE 8
| # | Q | # | Q | # | Q |
|---|---|---|---|---|---|
| 45 | 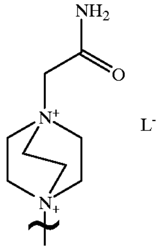 | 46 | 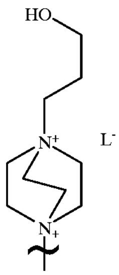 | 47 | 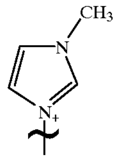 |
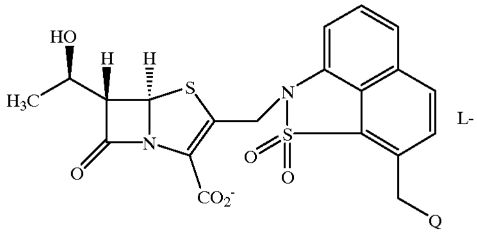
TABLE 9
| # | Q | # | Q | # | Q |
|---|---|---|---|---|---|
| 49 | 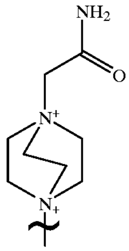 | 50 | 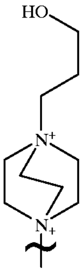 | 51 | 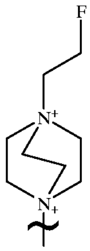 |
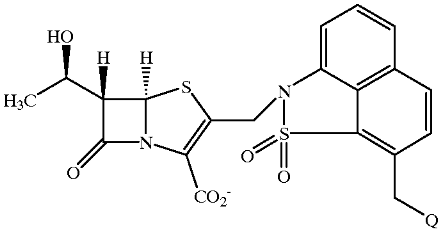
TABLE 10
| # | Q | # | Q | # | Q |
|---|---|---|---|---|---|
| 52 | 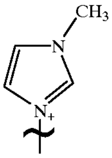 | 53 | 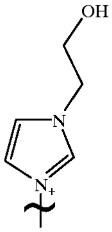 | 54 | 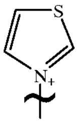 |
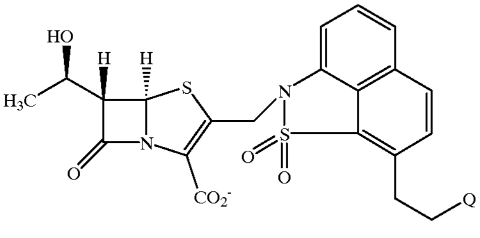

TABLE 11
| # | Q | # | Q | # | Q |
|---|---|---|---|---|---|
| 56 | 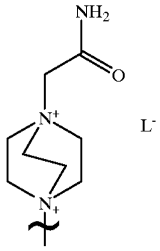 | 57 | 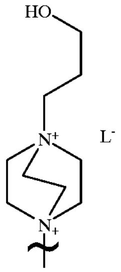 | 58 | 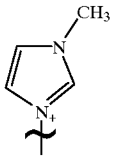 |
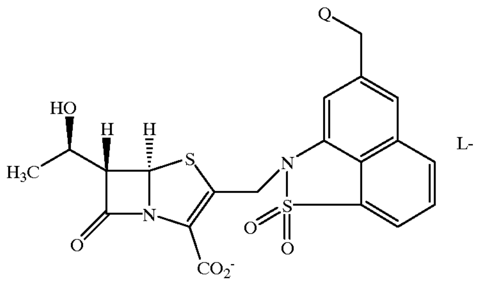
TABLE 12
| # | Q | # | Q | # | Q |
|---|---|---|---|---|---|
| 60 | 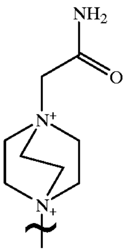 | 61 | 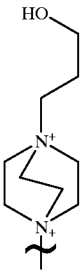 | 62 | 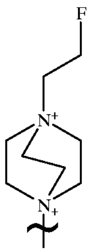 |
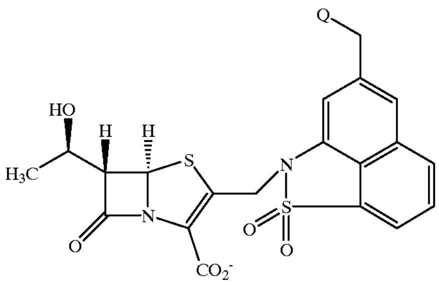
TABLE 13
| | | | | | |
|---|---|---|---|---|---|
| 63 | 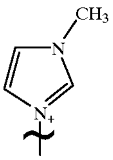 | 64 | 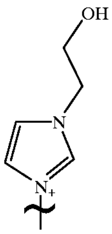 | 65 | 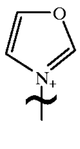 |
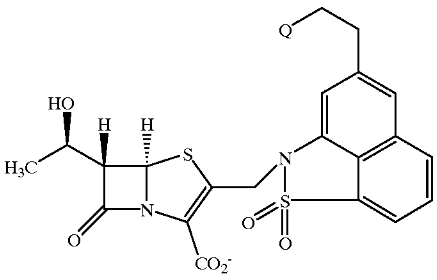

TABLE 14
| # | Q | # | Q | # | Q |
|---|---|---|---|---|---|
| 67 | 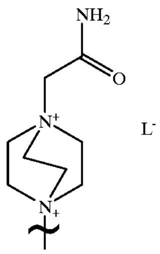 | 68 | 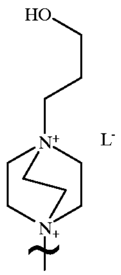 | 69 | 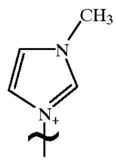 |
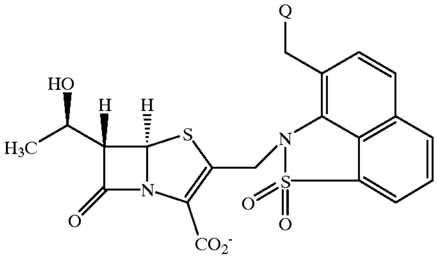
TABLE 15
| # | Q | # | Q | # | Q |
|---|---|---|---|---|---|
| 74 | 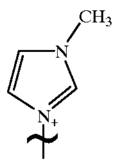 | 75 | 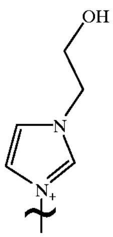 | 76 | 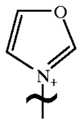 |
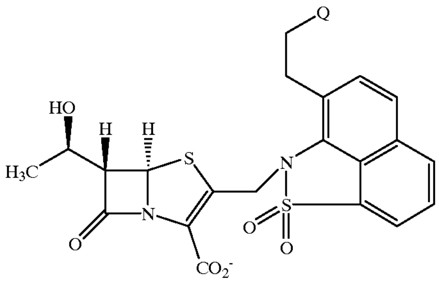

TABLE 16
| # | Q | # | Q | # | Q |
|---|---|---|---|---|---|
| 78 | 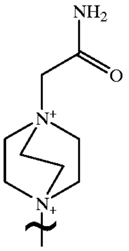 $L^-$ | 79 | 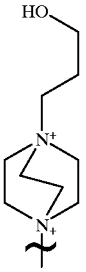 $L^-$ | 80 | 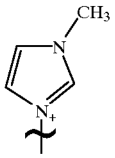 |
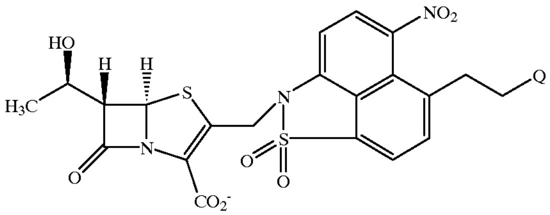
TABLE 17
| # | Q | # | Q | # | Q |
|---|---|---|---|---|---|
| 82 | 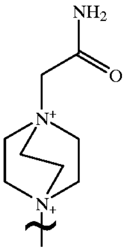 | 83 | 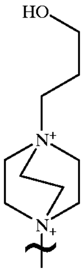 | 84 | 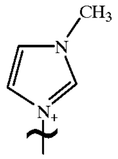 |
TABLE 18
| # | Q | # | Q | # | Q |
|---|---|---|---|---|---|
| 86 | 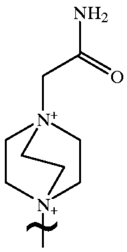 | 87 | 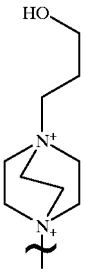 | 88 | 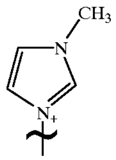 |
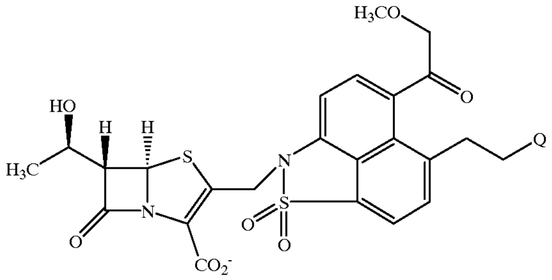
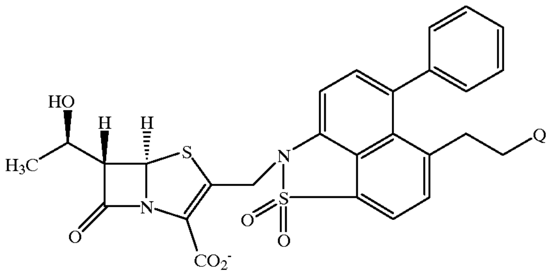

TABLE 19
| # | Q | # | Q | # | Q |
|---|---|---|---|---|---|
| 90 | 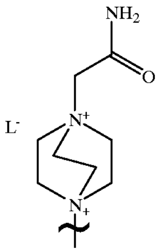 | 91 | 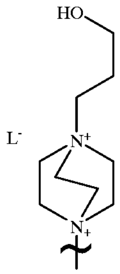 | 92 | 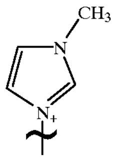 |
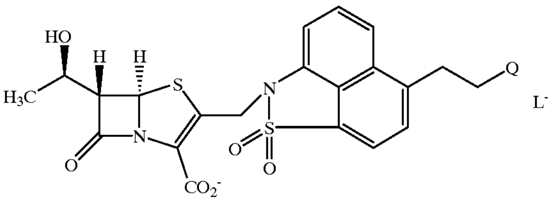
TABLE 20
| #93 | | #94 | | #95 | | #96 | |
|---|---|---|---|---|---|---|---|
| $R_2$ | Q | $R_2$ | Q | $R_2$ | Q | $R_2$ | Q |
| Cl | 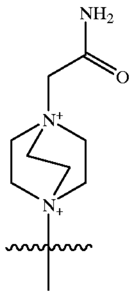 | $CH_3$ | 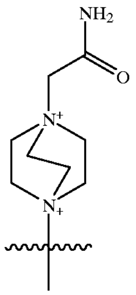 | Cl | 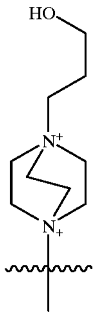 | $CH_3$ | 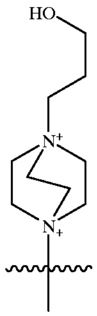 |
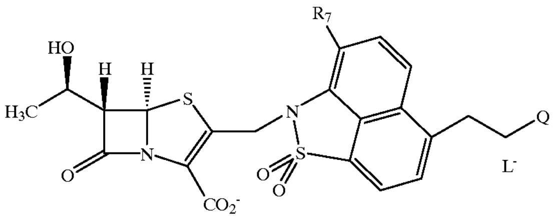

TABLE 21
| #97 | | #98 | | #99 | | #100 | |
|---|---|---|---|---|---|---|---|
| $R_7$ | Q | $R_7$ | Q | $R_7$ | Q | $R_7$ | Q |
| Cl | 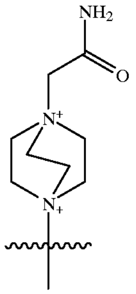 | $CH_3$ | 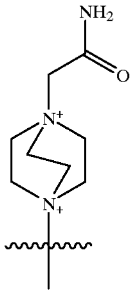 | Cl | 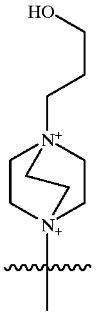 | $CH_3$ | 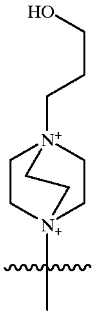 |
wherein Q is as defined in the tables and $L^-$ represents a pharmaceutically acceptable counterion.
26. A pharmaceutical composition comprised of a compound in accordance with claim 1 in combination with a pharmaceutically acceptable carrier.
* * * * *